(12) United States Patent
Sawynok et al.

(10) Patent No.: US 6,211,171 B1
(45) Date of Patent: Apr. 3, 2001

(54) USE OF ANTIDEPRESSANTS FOR LOCAL ANALGESIA

(75) Inventors: Jana Sawynok; Mike Esser; Allison Reid, all of Nova Scotia (CA)

(73) Assignee: Dalhousie University, Nova Scotia (CA)

( * ) Notice: Subject to any disclaimer, the term of this patent is extended or adjusted under 35 U.S.C. 154(b) by 0 days.

(21) Appl. No.: 09/081,709

(22) Filed: May 19, 1998

(51) Int. Cl.$^7$ .......................... A61K 31/55; A61K 31/50; A61K 31/495; A61K 31/335; A61K 31/135

(52) U.S. Cl. ................ 514/211.13; 514/211.08; 514/217; 514/254.06; 514/450; 514/649; 514/653; 514/656

(58) Field of Search ............... 514/254.04, 653, 514/221.08, 649, 656, 211.13, 450, 217

(56) References Cited

U.S. PATENT DOCUMENTS

| | | | |
|---|---|---|---|
| 3,491,188 | 1/1970 | Stoll et al. | 424/244 |
| 4,594,358 | 6/1986 | Hynes | 514/651 |
| 5,446,070 | * 8/1995 | Mantelle | 514/772.6 |
| 5,589,511 | 12/1996 | Young et al. | 514/646 |

FOREIGN PATENT DOCUMENTS

| | | | |
|---|---|---|---|
| 0 431 663 A1 | 11/1990 | (EP) | A61K/31/645 |
| 0 615 749 A2 | 3/1994 | (EP) | A61K/31/00 |
| WO 92/14453 | 9/1992 | (WO) | A61K/31/04 |
| WO 91/02527 | 3/1997 | (WO) | A61K/31/44 |
| WO 97/10815 | 3/1997 | (WO) | A61K/31/13 |

OTHER PUBLICATIONS

Ortega–Alvaro, et al., "The Effects of Different Monoaminergic Antidepressants on the Analgesia Induced by Spinal Cord Adrenal Medullary Transplants in the Formalin Test in Rats," *Anesth Analg.*, 84:816–820.

Sierralta, et al., "Effect of p–Chlorophenylalanine and α–Methyltyrosine on the Antinociceptive Effect of Antidepressant Drugs," *Pharmacology & Toxicology*, 77:276–280.

Ardid, et al., "Evidence for a central but not a peripheral analgesic effect of clomipramine in rats," *Pain*, 45:95–100 (1991).

Bianchi, et al., "Effects of chlomipramine and fluoxetine on subcutaneous carrageenin–induced inflammation in the rat," *Inflamm Res*, 44:466–469 (1995).

Esser and Sawynok, "Amitriptyline Decreases Thermal Hyperalgesia, But Not Mechanical Allodynia, In A Rat Model Of Neuropathic Pain," *Neuroscience Abstracts*, 23:1538 (1997).

Fletcher, et al., "Antinociceptive Effect of Bupivacaine Encapsulated in Poly(D,L))–Lactide–Co–Glycolide Microspheres in the Acute Inflammatory Pain Model of Carrageenin–Injected Rats," *Anesth Analg*, 84:90–94 (1997).

Max, M. B., "Antidepressants as Analgesics," *Progress in Pain Research and Management*, 1:229–246 (1194).

McQuay, et al., "A systematic review of antidepressants in neuropathic pain," *Pain*, 68:217–227 (1996).

Potter and Hollister, "Antidepressant Agents", *Basic & Clinical Pharmacology*, 7:483–495 (1998).

"Zonalon," *CPS*, 33:1911, (1998).

Chapleau and Gebhart, "Effect of Antidepressants on Mechanosensitive Pelvic Nerve Afferent Fibers Innervating the Colon of the Rat" *Gastroenterology* 112:A833 (1997).

Embase abstract, AN: 96229589, Lipman, 1996.*

* cited by examiner

Primary Examiner—D. Margaret Seaman
(74) Attorney, Agent, or Firm—Gray Cary Ware & Freidenrich LLP; Stephen E. Reiter; Sheila R. Kirschenbaum

(57) ABSTRACT

When administered locally, tricyclic, second generation and third generation antidepressants, such as amitriptyline and desipramine, have been shown to produce analgesia in a subject having a site of local discomfort. The analgesic effect of such antidepressants, when administered locally is equal to that achieved by systemic administration and lasts longer. The invention provides compositions containing tricyclic, second generation, and third generation antidepressants for local administration, such as those formulated for topical application, or for injection in slow release delivery vehicles, and methods for their use for producing local analgesia.

34 Claims, 25 Drawing Sheets

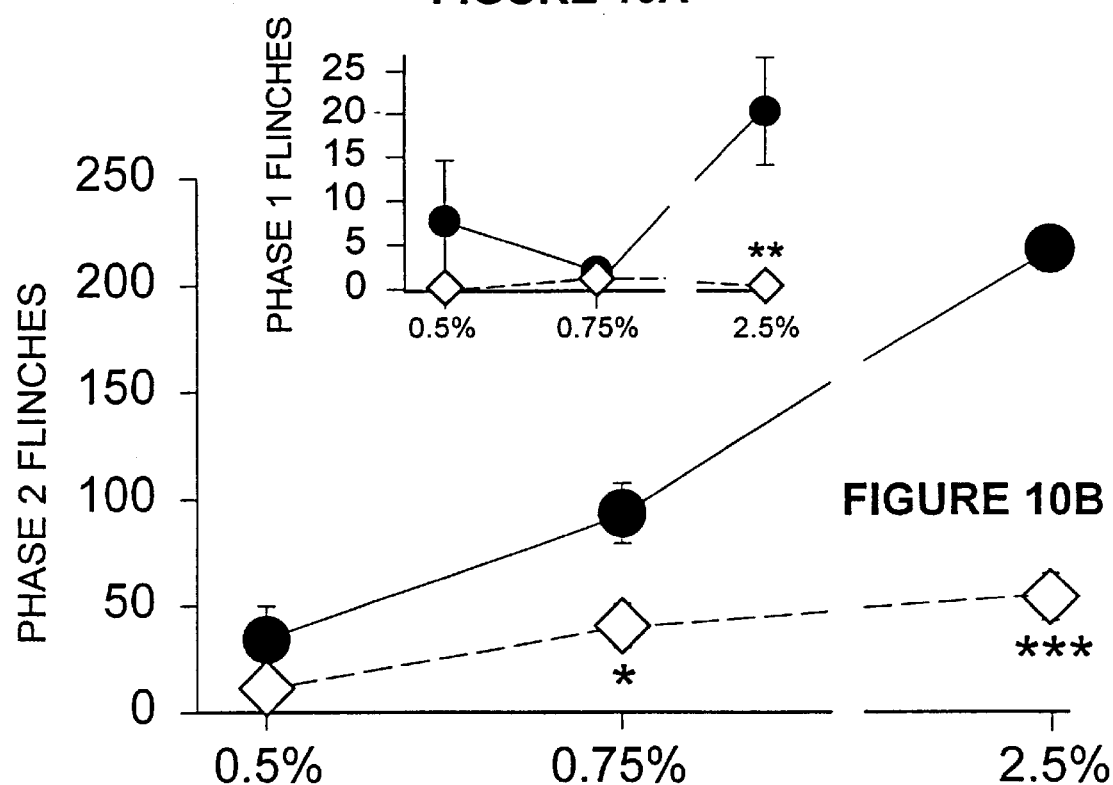
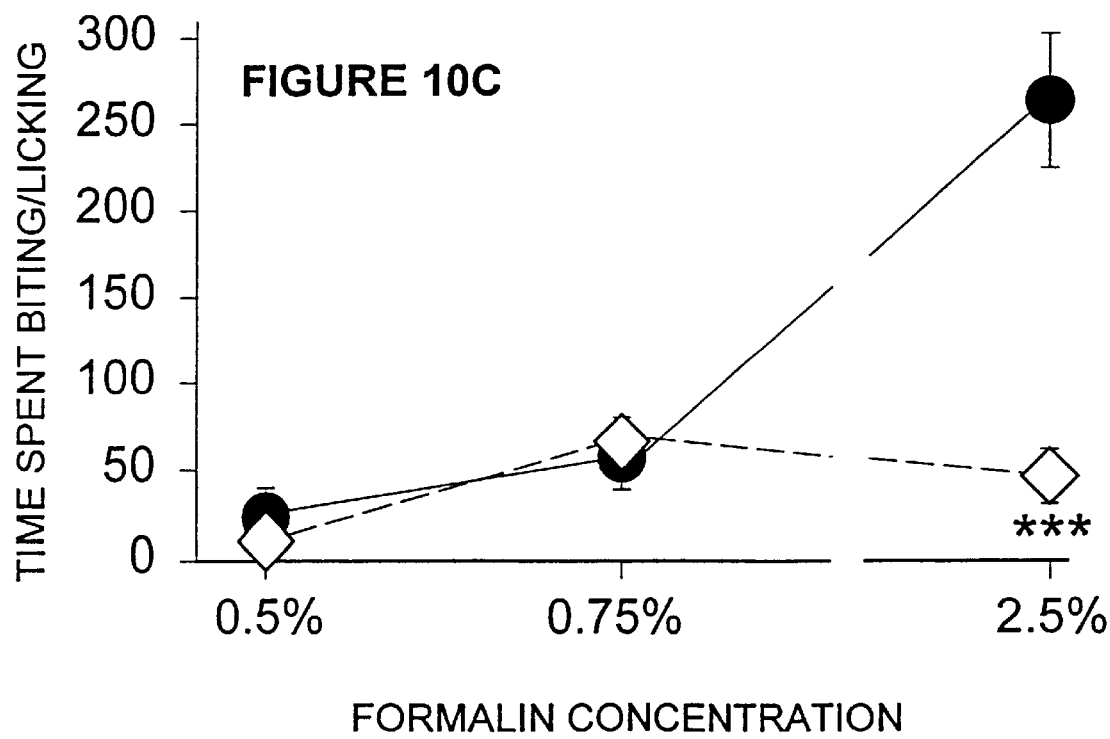

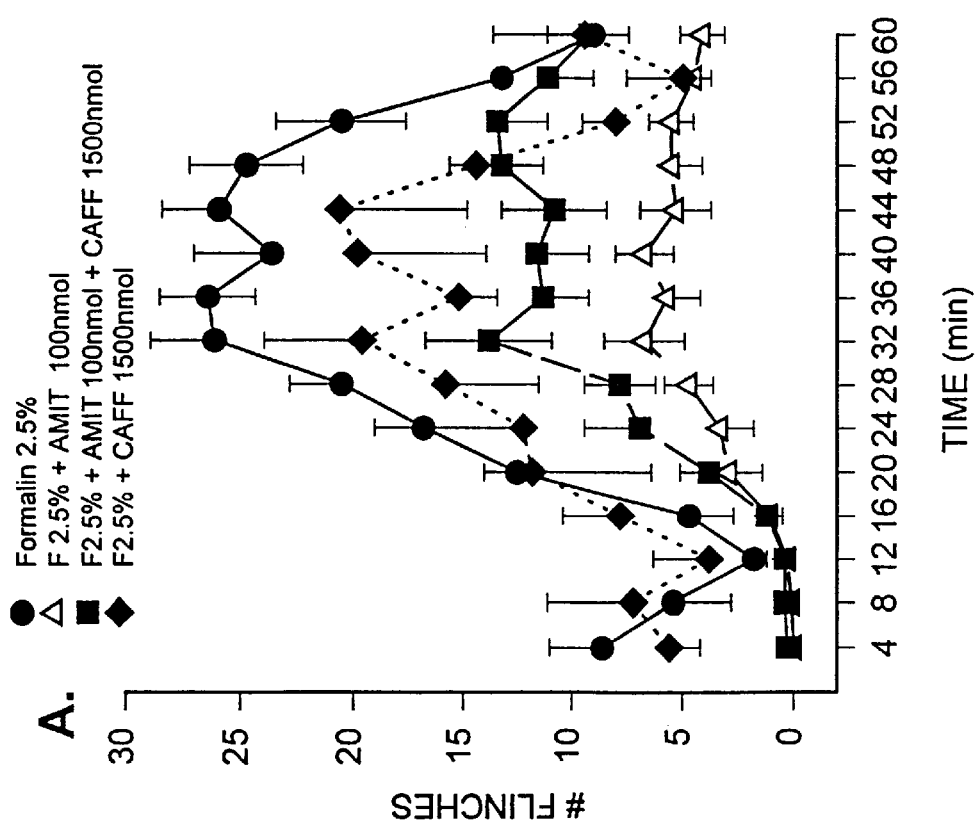
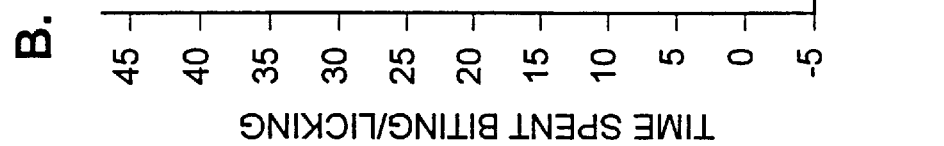
FIGURE 12A
FIGURE 12B

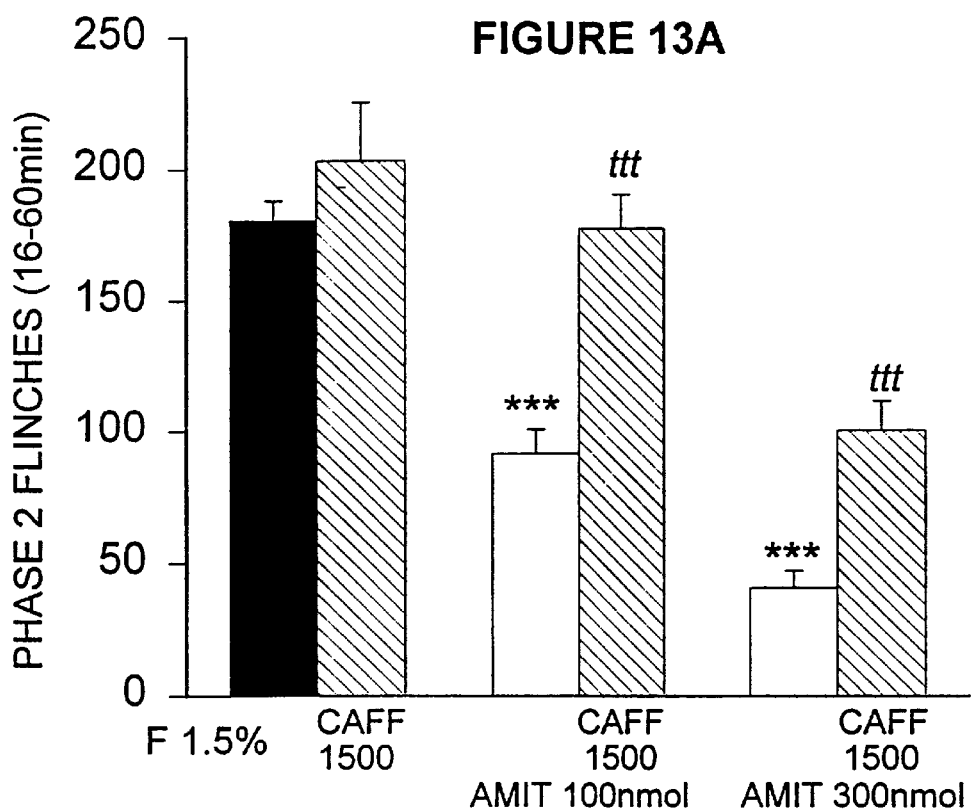
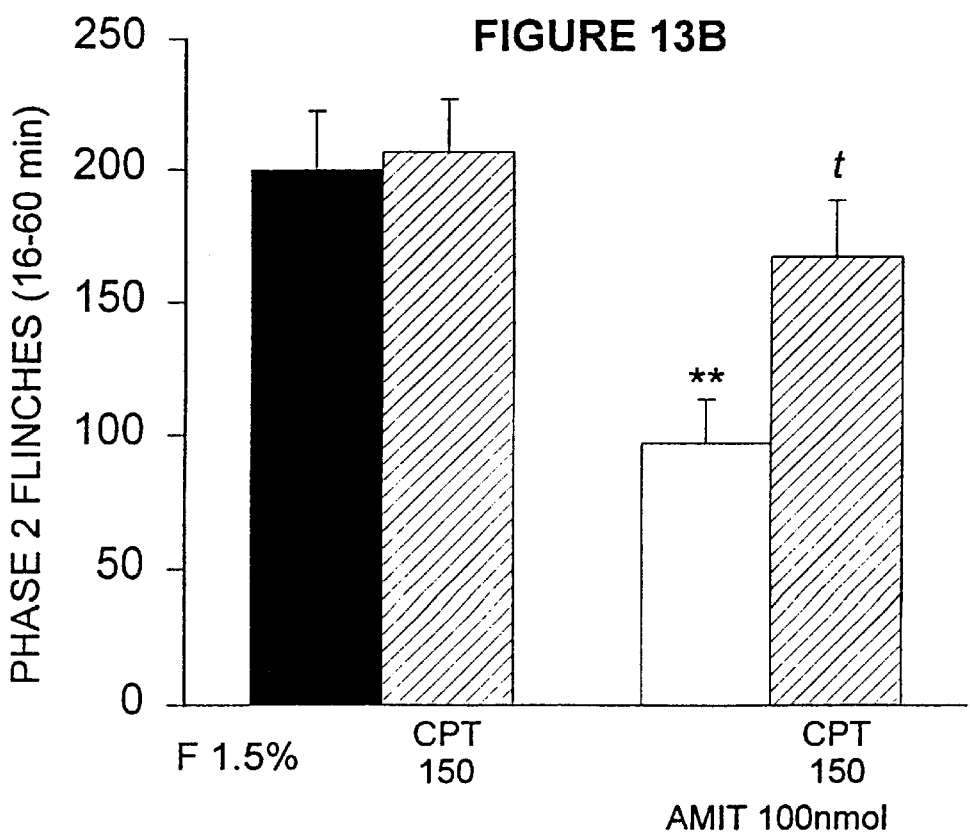

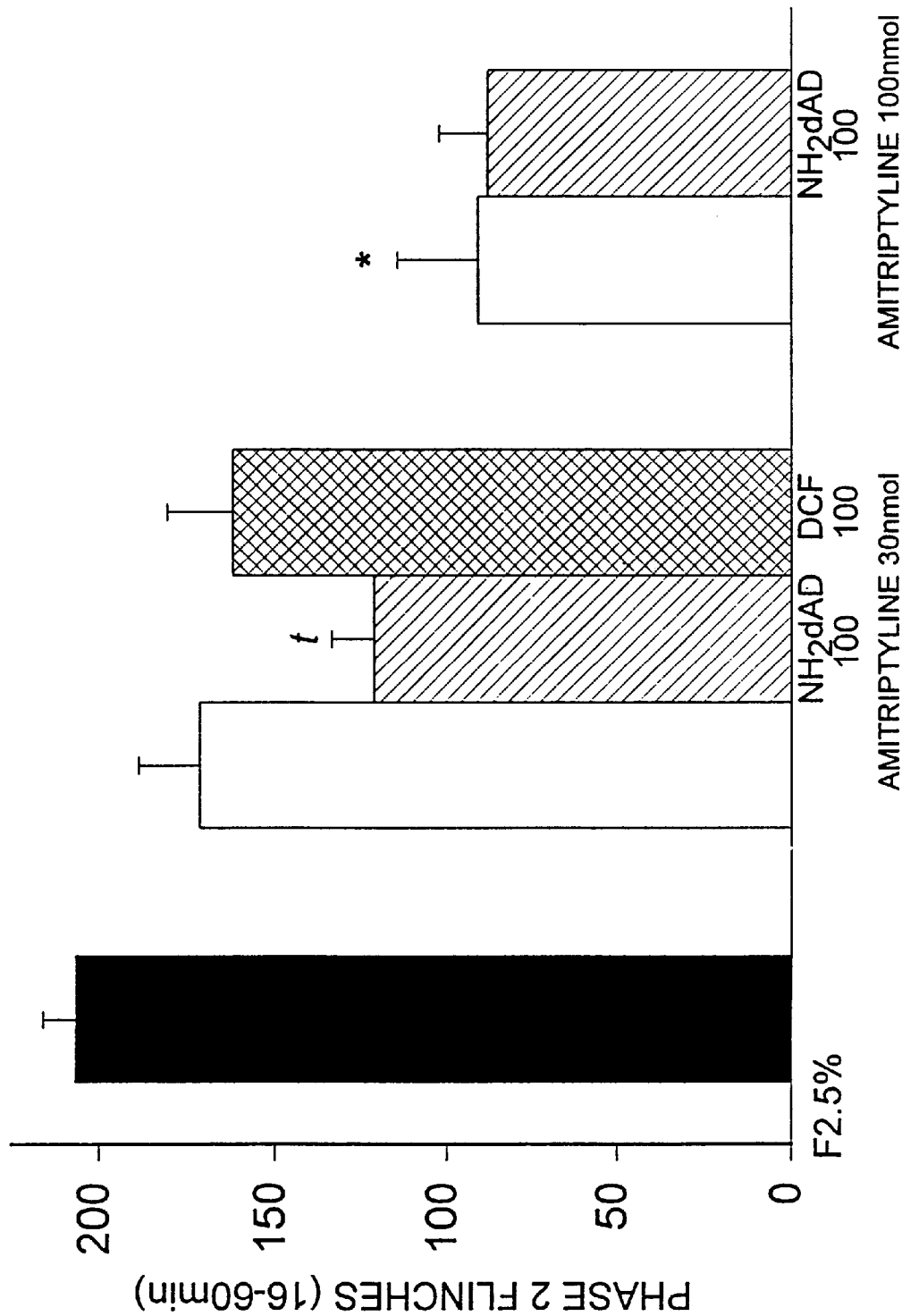

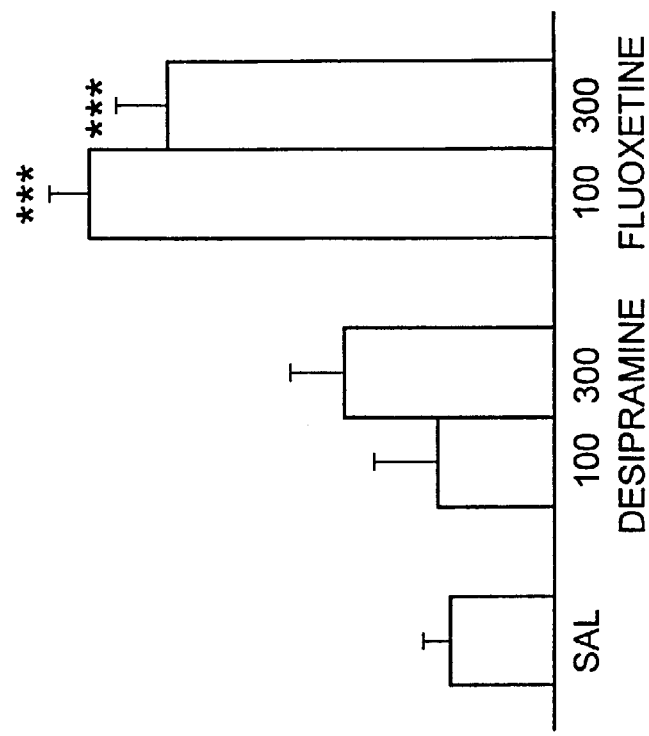
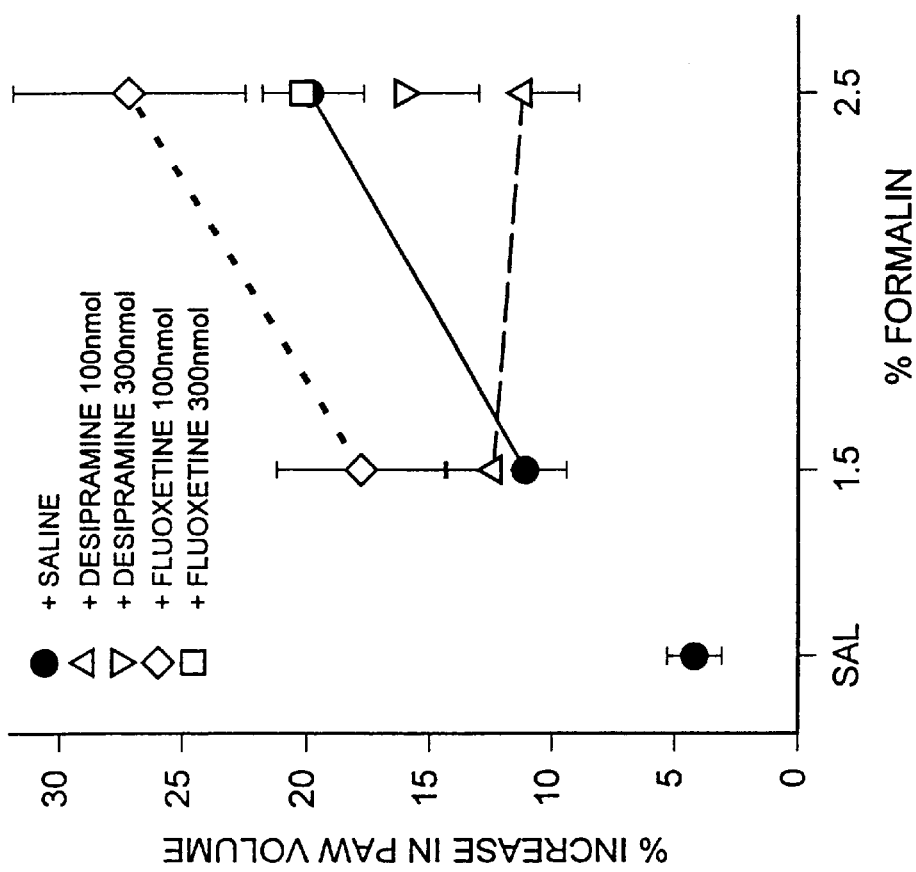
FIGURE 22B
FIGURE 22A

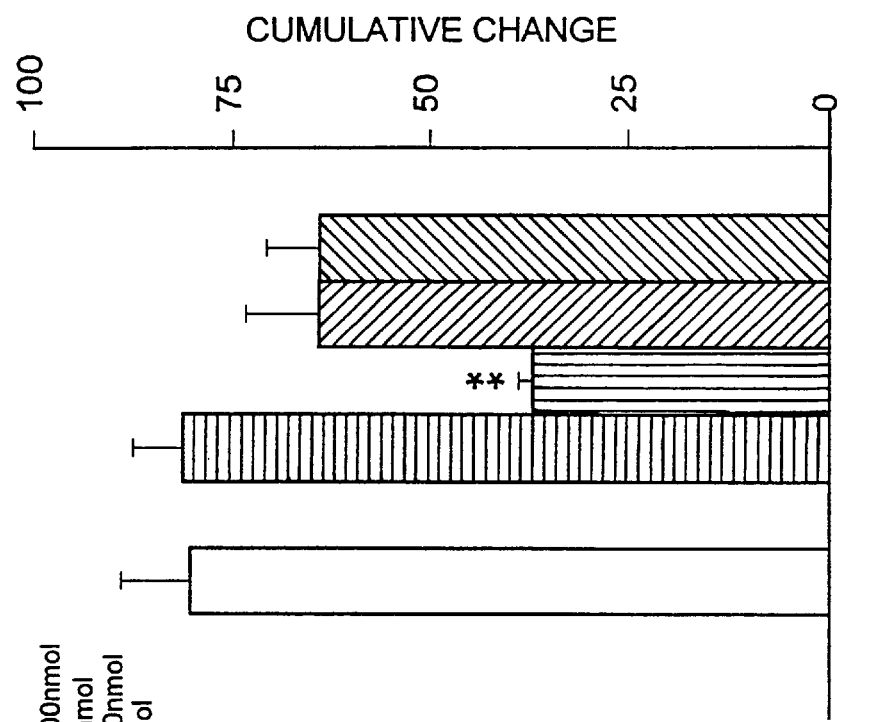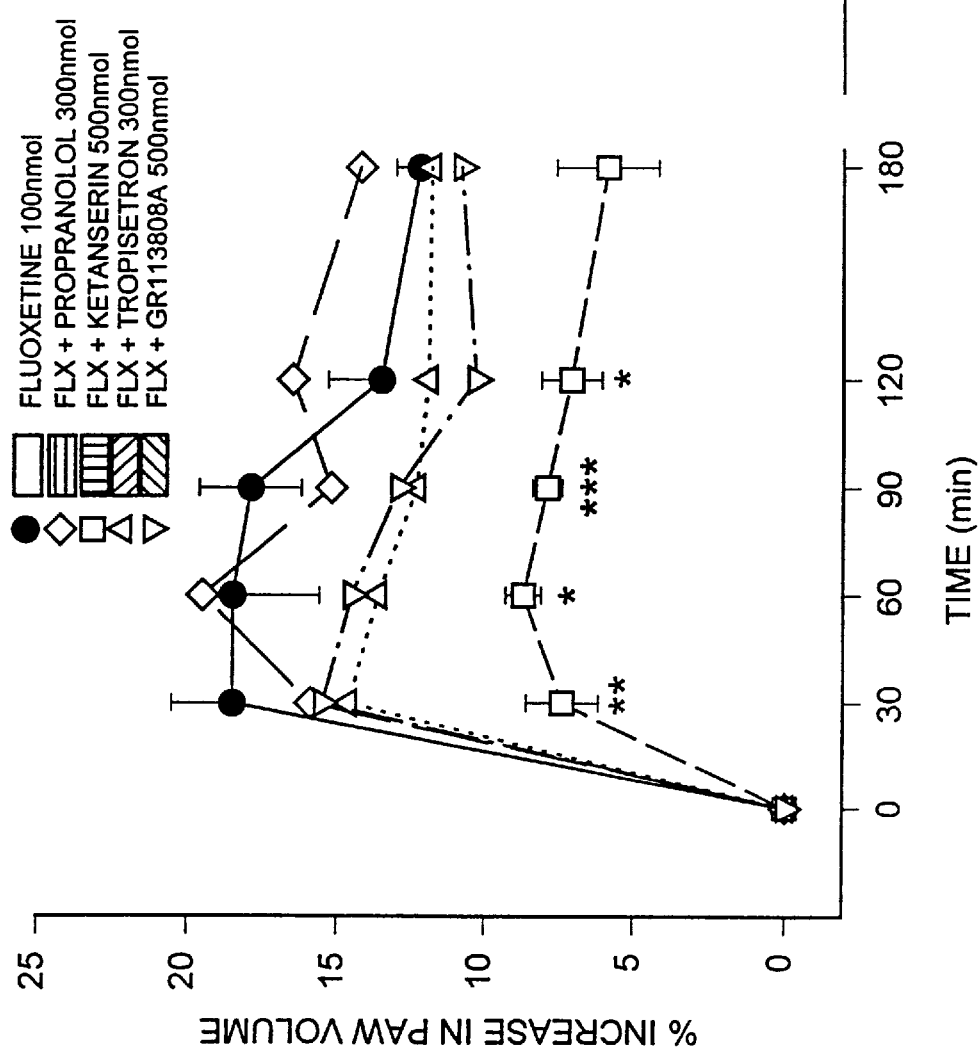
FIGURE 24A
FIGURE 24B

USE OF ANTIDEPRESSANTS FOR LOCAL ANALGESIA

FIELD OF THE INVENTION

The present invention relates to therapeutic compositions and methods for their use. In a particular aspect, the present invention relates to compositions for producing pain relief and methods of their use.

BACKGROUND OF THE INVENTION

Neuropathic pain is a form of chronic pain that can persist for months, years or decades following an injury, and results from damage to peripheral nerves, nerve roots, the spinal cord or certain brain regions. It differs from nociceptive pain in terms of duration, characteristics, underlying mechanisms and treatment (Bennett G. J. (1994a) In: *Textbook of Pain* (Ed. Wall P D, Melzack R) Churchill Livingstone, London 3rd edn, 201). Neuropathic pain can consist of spontaneous pain (e.g., burning, cutting, tingling), evoked pain (e.g., allodynia evoked by stimulation of non-nociceptive afferents, and hyperalgesia evoked by stimulation of nociceptive afferents) and paroxysmal pain (e.g., originating from a trigger point, described as stabbing, lancinating, shocklike) (Bennett G. J. (1994a) In: *Textbook of Pain* (Ed. Wall P D, Melzack R) Churchill Livingstone, London 3rd edn, 201). Neuropathic pain can accompany nociceptive pain, and multiple treatment strategies may be required for optimal alleviation of pain (Portenoy R. K. (1991) In: *Towards a New Pharmacology of Pain* (Ed. Basbaum A I, Besson J. M.) John Wiley & Sons Ltd, New York, 393; Devor M, Basbaum A. I., Bennett ., Blumeberg H, Campbell et al (1991) In: *Towards a New Pharmacotherapy of Pain* (Ed. Basbaum A I, Besson J. M.) John Wiley & Sons, New York, 417). Neuropathic syndromes are traditionally classified according to the disease or event that precipitated them (e.g., postherpetic neuralgia following shingles, causalgia following partial damage to a major nerve, central pain following a thalamic infarct) (Portenoy R. K. (1991) In: *Towards a New Pharmacology of Pain* (Ed. Basbaum A. I., Besson J. M.) John Wiley & Sons Ltd, New York, 393; Merskey H, Bogaduk N (1994) In: *Classification of Chronic Pain. Descriptions of Chronic Pain Syndromes and Definitions of Pain Terms,* 2nd edn, IASP Press, Seattle, page 40). The involvement of the sympathetic nervous system in a number of these conditions has been appreciated for some time. Pain syndromes with a sympathetic component are considered as sympathetically maintained pain (reflect sympathetic dystrophy, causalgia) (Bonica J. J. (1990) In: *The Management of Pain* (Ed. Bonica J. J.) Lea & Fibiger, Philadelphia 2nd edn. Bonica (1990, 220; Blumeberg H., J änig W. (1994) In: *Textbook of Pain* (Ed. Wall P D, Melzack R) Churchill Livingstone, London 3rd edn, 685).

Neuropathic pain is particularly difficult to treat clinically. The use of opioids is controversial, with issues of contention being the relative refractoriness of neuropathic pain compared to nociceptive pain, the need for higher doses with an increased incidence of side effects to achieve partial effects, and concerns over the long term use of opioids in a nonmalignant context (Arnér S, Meyerson B A (1988) *Pain* 22: 11; Kuypers H., Konig H., Adriaenson H., Gybels J. M. (1991) *Pain* 47: 5; Portenoy R. K., Foley K. M., Inturrisi C. E. (1990) *Pain* 43: 273; Portenoy R. K. (1994) In: *Progress in Pain Research and Management* (Ed. Fields H. L., Liebskind J. C.) IASP Press, Seattle, 247). The major classes of agents currently used to treat neuropathic pain include systemically delivered antidepressants, anticonvulsants, local anesthetics, and specialized agents such as muscle relaxants, and sympatholytic drugs (reviewed Portenoy R. K. (1991) In: *Towards a New Pharmacology of Pain* (Ed. Basbaum A I, Besson J. M.) John Wiley & Sons Ltd, New York, 393; Portenoy R. K. (1993) *Drug Therapy* 23: 41; Max M B (1994) In: *Progress in Pain Research and Management* (Ed. Fields H. L., Liebskind J. C.) IASP Press, Seattle, 229). However, many of these treatments show limited effectiveness (complete pain relief is rarely achieved), and there is a high incidence of debilitative side effects (Portenoy R. K. (1993) *Drug Therapy* 23: 41; Bennett G. J. (1994a) In: *Textbook of Pain* (Ed. Wall P D, Melzack R) Churchill Livingstone, London 3rd edn, 201; Mac Farlane et al., (1997) *Pharmacol. Ther.* 75:1).

Damage to nerves can activate changes in both the peripheral and central nervous systems, and these lead to the characteristic expression of neuropathic pain. Peripherally, the following mechanisms may be involved (reviewed by Devor M, Basbaum A I, Bennett G. J., Blumeberg H, Campbell et al (1991) In: *Towards a New Pharmacotherapy of Pain* (Ed. Basbaum A I, Besson J. M.) John Wiley & Sons, New York, 417; Devor M (1994) In: *Textbook of Pain* (Ed. Wall P D, Melzack R) Churchill Livingstone, London, 3rd edn, 79; Blumeberg H, Jänig W (1994) In: *Textbook of Pain* (Ed. Wall P D, Melzack R) Churchill Livingstone, London 3rd edn, 685). (1) Following injury, normally silent nociceptors become sensitized and acquire an ongoing spontaneous activity, a lowered threshold for activation, and a heightened response to suprathreshold stimulation. (2) Development of ectopic discharges can occur at the site of injury, site of regeneration and neuroma formation, or within the dorsal root ganglion. (3) Following injury, sympathetic afferents can excite sensory nerve endings, regenerating nerve sprouts, neuromas, and the dorsal root ganglion cell. Central mechanisms implicated in neuropathic pain are as follows (Coderre et al., (1993) *Pain* 52:259; Bennett (1994) In: *Textbook of Pain* (ed. by P. D. Wall et al., London, 3rd edn., 201; Woulff and Doubell (1994) *Curr. Opin. Neurobiol.* 4:525): (1) Transmission neurons within the spinal cord exhibit enhanced sensitivity to excitation by excitatory amino acids (EAAs) and substance P (SP). This condition leads to allodynia (following AB fibre activation) and hyperalgesia (following Aδ and C fibre activation). (2) Disinhibition resulting from loss of inhibitory input to projection neurons and an aberrant patterning of responses to large diameter afferent activation. (3) Myelinated afferents, which normally would enervate deeper laminae, projecting into and making synaptic connections in more superficial laminae. This can be a mechanism for the generation of allodynia.

A number of models of neuropathic pain have been developed in order to provide a basis for understanding of neuropathic changes that occur following nerve injury, and to provide model systems in which to test novel therapeutic strategies (reviewed Bennett G. J. (1994b) In: *Progress in Pain Research and Management* Vol 2 (Ed. Gebhart C F, Hammond D L, Jensen T S) IASP Press, Seattle, 495). The best characterized are a number of nerve injury models which have been developed only relatively recently (chronic constriction injury due to loose ligation of the sciatic nerve, Bennett G. J., Xie Y. K. (1988) *Pain* 33: 87; and partial sciatic ligation due to tight ligation of a portion of the sciatic nerve (Seltzer et a. (1990) *Pain* 43:205) and tight ligation of two spinal nerves (Kim S. H., Chung J. M. (1992) *Pain* 50: 355)). These model systems exhibit various manifestations of neuropathic pain (e.g., degree of expression of spontaneous pain behaviors, mechanical or thermal allodynia, mechanical or thermal hyperalgesia) and degree of sympathetic nerve involvement (Neil A, et al. (1991) *Brain Res* 565: 237; Shir Y., Seltzer Z. (1991) *Pain* 45: 309; Kim S H, Na H S, Sheen Ki, Chung J M (1993) *Pain* 55: 85; Kim K J, Yoon Y W, Chung J M (1997) *Exp Brain Res* 113: 200). The spinal nerve ligation (SNL) model exhibits a greater degree of evoked pain (mechanical allodynia) and of sympathetic involvement in this parameter than do the partial sciatic ligation or chronic constriction injury models, while the chronic constriction injury model exhibits a greater degree of spontaneous pain. It is however appreciated that such properties may be relative and change with time (i.e., sympathetic dependency can change with time both in animal models and in clinical neuropathic pain, Staton-Hicks M, Jänig W, Hassenbusch S, Haddox J D, Boas R, Wilson P (1995) *Pain* 63: 127).

Systemically administered antidepressants offer an alternate therapy in neuropathic and chronic pain states. Interactions with biogenic amines, endogenous opioids, excitatory amino acid receptors, substance P and calcium and sodium channels have been considered in efforts to pinpoint the mechanism of systemically administered antidepressants (reviewed by Eschalier A, Mestre C, Dubray C, Ardid D (1994) *CNS Drugs* 2: 261). What is clear is that antidepressants can act at both supraspinal (Spiegel, K., Kalb, R. and Pasternak, G. W., *Ann. Neurol.* 13 (1983) 462–465, Eschalier A, Mestre C, Dubray C, Ardid D (1994) *CNS Drugs* 2: 261) and spinal (Hwang, A. S. and Wilcox, G. L., *Pain* 28 (1987) 343–355; Iwashita, T. and Shimizu, T., *Brain Research* 581 (1992) 59–66; J. Eisenachand G. F.Gebhart, *Anesthesiology* 83 (1995) 1046–1054) sites of action.

This analgesic action is independent of antidepressant effects as it occurs in non-depressed subjects and occurs independently of mood changes in depressed subjects (Magni G (1991) *Drugs* 42: 730; Onghena P, Van Houdenhove B (1992) *Pain* 49: 205; Max M B (1994) In: *Progress in Pain Research and Management* (Ed. Fields H L, Liebskind J C) IASP Press, Seattle, 229, McQuay H J, Tramer M, Nye B A, Carroll D, Wiffen P J, Moore R A (1996) *Pain* 68: 217). Agents which block the uptake of both noradrenaline (NA) and 5-hydroxytryptamine (5-HT) such as amitriptyline, or which block NA but not 5-HT, such as desipramine, are more effective than those with selectivity for 5-HT, such as fluoxetine (Max M B (1994) In: *Progress in Pain Research and Management* (Ed. Fields H L, Liebskind J C) IASP Press, Seattle, 229). Pain relief is reported to be apparent within one week of therapy (McQuay H J, Carroll D, Glynn C J (1992) *Anaesthesia* 47: 646). This time course corresponds to the time required to attain stable plasma levels (t½ 17–36 hours in humans, Ziegler V E, Biggs J T, Aardekani A B, Rosen S H (1978) *J Clin Pharmacol* 18: 462). By contrast, the antidepressant activity of these compounds takes 4–6 weeks to become apparent (Potter W Z, Rudorfer M, Manji H (1991) *New Eng J Med* 325: 633). These differences in profile of active drugs, time course, and independent expression of effects suggest that mechanisms underlying pain relief and alleviation of depression differ.

In animal tests, both the systemic and spinal administration of antidepressants show intrinsic efficacy in a number of nociceptive pain tests, and augment analgesia produced by opioids (reviewed by Eschalier A, Mestre C, Dubray C, Ardid D (1994) *CNS Drugs* 2: 261). However, this profile can be variable, and inhibitory effects on the action of morphine have been observed in some cases (reviewed by Eschalier et al., supra). Methodological issues (e.g., test paradigm, intensity of stimulus, dose, regimen of acute versus chronic administration) are reported to account for many of these differences (Kellstein D E, Malseed R T, Goldstein F J (1984) *Pain* 60: 275; Kellstein D E, Malseed R T, Ossipov M H, Goldstein F J (1988) *Neuropharmacology* 27: 1; Fialip J, MartyH, Makambila M C, CiViate M A, Eschalier A (1989) *J Pharmacol Exp Ther* 248: 747). Systemically administered antidepressants also exhibit intrinsic actions in a number of neuropathic pain tests including nerve transaction (Seltzer Z, Tal M, Sherav Y (1989) *Pain* 37: 245), mononeuropathy (Ardid D, Gilbaud G (1992) *Pain* 49: 279) and diabetic neuropathy models (C.Courteix et al. (1994) *Pain* 57:153–160). One study examined chronic versus acute dosing regimens (Ardid D, Gilbaud G (1992) *Pain* 49: 279), and observed that the activity seen following chronic paradigms appeared to be accounted for by accumulating doses rather than being qualitatively different.

SUMMARY OF THE INVENTION

In accordance with the present invention, it has been discovered that locally administered tricyclic, second generation, or third generation antidepressant(s) produce a local antinociceptive action, especially against inflammatory and neuropathic pain. When administered locally in animal models of inflammatory (formalin test) and neuropathic pain (spinal nerve ligation), amitriptyline, a non selective noradrenaline (NA) and 5-hydroxytryptamine (5-HT) reuptake inhibitor, and desipramine, a selective NA reuptake inhibitor, produced local antinociceptive actions.

Accordingly, in one aspect of the invention, there are provided compositions containing an effective therapeutic amount of a tricyclic, second generation or third generation antidepressant in an inert carrier. The compositions are preferably formulated for local administration, for example in a saline solution, or as a cream, gel, ointment, or spray.

Such formulations possess the advantage that a higher and more efficacious concentration of the antidepressant can be attained in the region of the sensory nerve terminal than with systemic administration of the antidepressant. In addition, local administration greatly reduces the side effects that result from systemic administration of tricyclic, second generation or third generation antidepressant(s).

In another aspect of the invention, there are provided methods for producing local analgesia in a subject having a site of local discomfort, such as is caused by inflammatory or neuropathic conditions. In the invention method, local analgesia is obtained by locally administering an effective amount of a tricyclic, second generation or third generation antidepressant to the site of discomfort, for example by injection, supersonic powder injection, transdermal electropotation, topical application, or encapsulation in a slow release delivery vehicle.

BRIEF DESCRIPTION OF THE FIGURES

FIG. 2C illustrates the cumulative change in the Maximum Possible Effect (ΔMPE) time course for ipsilateral (ipsi) and contralateral (contra) paws, with open bars representing saline control, bars with rightward sloping lines representing 1 mg/kg AMIT, bars with leftward sloping lines representing 3 mg/kg AMI, and bars with crosshatching representing 10 mg/kg AMI. Values represent the MPE∓s.e.m. (n=5 for 1 and 3 mg/kg, and n=15 for 10 mg/kg). *=P<0.05 compared to saline controls.

FIG. 3C represents the cumulative change in the MPE (ΔMPE) time course in ipsilateral (ipsi) and contralateral (contra) paws, with open bars representing saline control, rightward sloping bars representing 100 nmol AMI (ipsi), and leftward sloping bars representing 100 nmol AMI (contra). Values represent the MPE∓s.e.m. (n=6 for both groups). *=P<0.05 compared to saline controls.

FIG. 4A shows the effect in the ipsilateral paw when the antidepressant is injected into the nerve-injured paw (ipsi) and non-injured paw (contra), and FIG. 4B shows the time course of the change in the thermal withdrawal latency in the contralateral paw, when the antidepressant is injected into the nerve injured paw (ipsi) and non-injured paw (contra), with ●=saline control; ■=AMI ipsi, and; ▲=AMI contra. FIG. 4C depicts the cumulative change in MPE value (ΔMPE), with open bars representing saline control (ipsi), bars with rightward sloping lines representing 100 nmol AMI (ipsi), and bars with leftward sloping lines representing 100 nmol AMI (contra). Values represent the MPE∓s.e.m. (n=9 for all groups). *=P<0.05 as compared to saline controls, t=P<0.01 as compared to contralateral controls.

FIG. 5C represents the cumulative change in the MPE (ΔMPE), with open bars representing saline control, bars with rightward sloping lines representing 1.5 mg/kg AMI, bars with leftward sloping lines representing 5 mg/kg AMI, and bars with crosshatching representing 10 mg/kg AMI. Values represent MPE∓s.e.m. (n=5 for 1.5 and 5 mg/kg, and n=15 for 10 mg/kg). *=P<0.05 as compared to saline, t=P<0.05 as compared 1.5 and 5.0 mg/kg.

FIG. 6C illustrates the cumulative change in the MPE (ΔMPE), ), with open bars representing saline control; bars with rightward sloping lines representing 30 µg AMI, bars with leftward sloping lines representing 60 µg AMI, and bars with crosshatching representing 90 µg AMI. Values represent the MPE∓s.e.m. (n=3 for 30 µg and 90 µg, and n=5 for 60 µg). *=P<0.05 compared to saline controls.

FIG. 7A illustrates the effect in the ipsilateral paw when the antidepressant is injected locally into the nerve-injured paw (ipsi) and non injured paw (contra). FIG. 7B illustrates the time course of the change in the mechanical threshold of the contralateral paw following injection into the nerve-injured paw (ipsi) and the non-injured paw (contra), with ●=saline control; ■=AMI (ipsi), and; ▲=AMI (contra). FIG. 7C illustrates the cumulative change in the value of MPE (ΔMPE) over the entire time course), with open bars representing saline control (ipsi), bars with rightward sloping lines representing 100 nmol AMI (ipsi), and bars with leftward sloping lines representing 100 nmol AMI (contra). Values represent the MPE∓s.e.m. (n=9 for all groups). *=P<0.05 as compared to saline controls, and t=P<0.01 as compared to contralateral controls.

FIGS. 10A–C are a series of graphs illustrating the inhibitory effect on phase 1 flinches (FIG. 10A), phase 2 flinches (FIG. 10B), and time spent biting and licking (FIG. 10C) following coadministration to rats of amitriptyline (100 nmol) (open diamonds) on formalin-induced behaviors at different concentrations of formalin (filled circles). n=6–11 per group. *=P<0.05, =P<0.01, and *=P<0.001 compared to the formalin only group.

FIGS. 12A–B are two graphs illustrating the time course of caffeine (CAFF) reversal of amitriptyline (AMI) action in the 2.5% formalin (F) test for the experiment illustrated in FIGS. 4A–C as measured by number of flinches (FIG. 12A) and time spent biting and licking (FIG. 12B). ●=2.5% formalin alone; open upward-pointing triangle=2.5% F+100 nmol AMIT; ■2.5% F+100 nmol AMI+1500 nmol CAFF; ◆=2.5% F+1500 nmol CAFF. Values depict group means (n=5–11 per group); error bars for s.e.m. were omitted in the interest of clarity.

FIGS. 13A–B are graphs illustrating the reversal of the antinociceptive action of amitriptyline (AMI) against 1.5% formalin (F) by caffeine (CAFF) (FIG. 13A), and 8-cyclopentyl-1,3-dimethylxanthine (CPT) (FIG. 13B). n=5–6 per group. =P<0.01, *=P<0.001 compared to formalin alone; t=P<0.05, ttt=P<0.001 compared to formalin/amitriptyline. The filled bars represent the effect of administering 1.5% formalin alone; the bars with downward sloping lines represent CAFF alone or in combination with AMIT, and the open bars represent the effect of AMI alone.

FIG. 14 is a bar graph illustrating enhancement of the local antinociceptive of 30 nM and 100 nM amitriptyline (open bars) against 2.5% formalin (filled bar) action as measured by decrease in phase 2 flinches in the formalin test by coadministration of the adenosine kinase inhibitor $NH_2dAD$ (100 nmol) (bars with rightward sloping lines), but not by the adenosine deaminase inhibitor 2'-deoxycoformycin (DCF) (100 nmol) (bars with cross hatching). n=6–8 per group. *=P<0.05 compared to formalin alone; t=P<0.05 compared to the formalin/amitriptyline combination.

FIGS. 17A and 17B show amelioration of phase 1 and phase 2 flinching behaviors, respectively, and FIG. 17C shows amelioration of biting/licking behaviors induced by formalin 2.5% (■) injected into the dorsal hindpaw of the rat when the formalin is coadministered with desipramine (DES) or fluoxetine (FLUOX) into the dorsal hindpaw (local effect) or injected into the contralateral hindpaw (systemic effect).▲= ipsilateral DES; open triangle=contralateral DES; ●=ipsilateral FLUOX; ○=contralateral FLUOX. Data depicts mean ∓s.e.m. for n=5–6; n=8 for ipsilateral control). *=P<0.05, =<0.01, *=P<0.001 compared to corresponding formalin group.

FIGS. 18A and 18B show the time course for the suppression of flinching behaviors by coadministration of DES with the formalin into the ipsilateral (FIG. 18A) or contralateral (FIG. 18B) paw. FIGS. 18C and 18D show the time course for suppression of biting/licking, behaviors after administration of the highest doses injected into the ipsilateral (FIG. 18C) or contralateral (FIG. 18D) paw. Values are means, with error bars omitted in the interest of clarity. Data corresponds to FIG. 17.

FIG. 19A depicts the local antinociceptive action of desipramine, but not fluoxetine, when injected into the ipsilateral (ipsi) paw corresponding to the spinal nerve ligation, and FIG. 19B depicts the lack of effect in the contralateral paw (contra) with ■=saline control; ●=DES; and ▲=FLUOX. FIG. 19C shows the cumulative change in MPE with the open bars representing saline control, the rightward sloping bars representing DES and the leftward sloping bars representing FLUOX. n=9 per group. *=P<0.05 compared to saline group.

FIG. 20A shows the anti-hyperalgesia MPE over time wherein ●=100 nmol DES; ■=1500 nmol CAFF; and ▲=DES+CAFF. FIG. 20B shows the cumulative change in MPE (ΔMPE) wherein the open bar represents 100 nmol DES; the bar with rightward sloping lines represents 1500 nmol CAFF; and the bar with crosshatching represents DES+CAFF. n=9 per group; *=P<0.05 compared to saline group.

FIG. 21A shows the effect on phase 1 flinches, and FIG. 21B shows the effect on phase 2 flinches. FIG. 21C shows the effect phase 2 biting/licking time. The empty bar represents the saline control; the bar with rightward sloping lines represents the effect of caffeine (CAFF) either alone or in combination with the test drug. Values depict mean∓s.e.m. for n=6 per group. *=P<0.05, =P<0.01, *=P<0.001 compared to formalin group. NS indicates no significant difference from corresponding antidepressant group.

FIGS. 22A–B are graphs illustrating the effect of locally administered desipramine and fluoxetine on paw volume in the presence of formalin. FIG. 22A shows the effect of saline (control), desipramine, or fluoxetine on paw volume following coadministration with formalin into the ipsilateral paw in the presence of formalin. ●=formalin+saline; open diamond=formalin+100 nmol FLUOX; open downward pointing triangle=formalin+300 nmol DES; and open square=formalin+300 nmol FLUOX. FIG. 22B shows the effect on paw swelling of desipramine or fluoxetine injected at either concentration used in FIG. 22A into the contralateral hindpaw (systemic effect). Paw volumes were determined at the end of the behavioral observation period. n=5–6 per group. ***=P<0.001 compared to the saline-treated group.

FIG. 23A shows the effects of 100 nmol DES (open diamond) and 300 nmol DES (open square). FIG. 23B shows the effects of 10 nmol FLUOX (open upward facing triangle); 30 nmol FLUOX (open downward-facing triangle), 100 nmol FLUOX (open diamond), and 300 nmol FLUOX (open square). FIG. 23C shows the effects of 100 nmol (open triangle) and 300 nmol (open square) amitriptyline on dorsal paw volume. n=6 per group. *=P<0.05, ***=P<0.001 compared to the saline-injected group.

FIGS. 24A–B are graphs illustrating the effects of the selective 5-HT receptor antagonists propranolol (5-HT$_1$), ketanserin (5-HT$_2$), tropisetron (5-HT$_{3/4}$) and GR113808A (5-HT$_4$) on the increase in paw volume induced by local injection of fluoxetine (FLX) (100 nmol). FIG. 24A shows the percent increase in paw volume over a three hour period of 100 nmol FLX alone (●); FLX+300 nmol propranolol (open diamond); FLX+500 nmol ketanserin (□), FLX+300 nmol tropisetron (open upward-pointing triangle); and FLX+500 nmol GR113808A (open downward-pointing triangle). FIG. 24B shows the cumulative effect of the increase of FIG. 24A over the same time period wherein the open bar represents FLX alone; the bar with horizontal lines illustrates FLX+propranolol; the bar with vertical lines illustrates FLX+ketanserin; the bar with rightward sloping lines represents FLX+tropisetron; and the bar with leftward sloping lines represents FLX+GLR113808A. n=5 per group. *=P<0.05, =P<0.01, *=P<0.001 compared to the fluoxetine group.

DETAILED DESCRIPTION OF THE INVENTION

Figure 1:
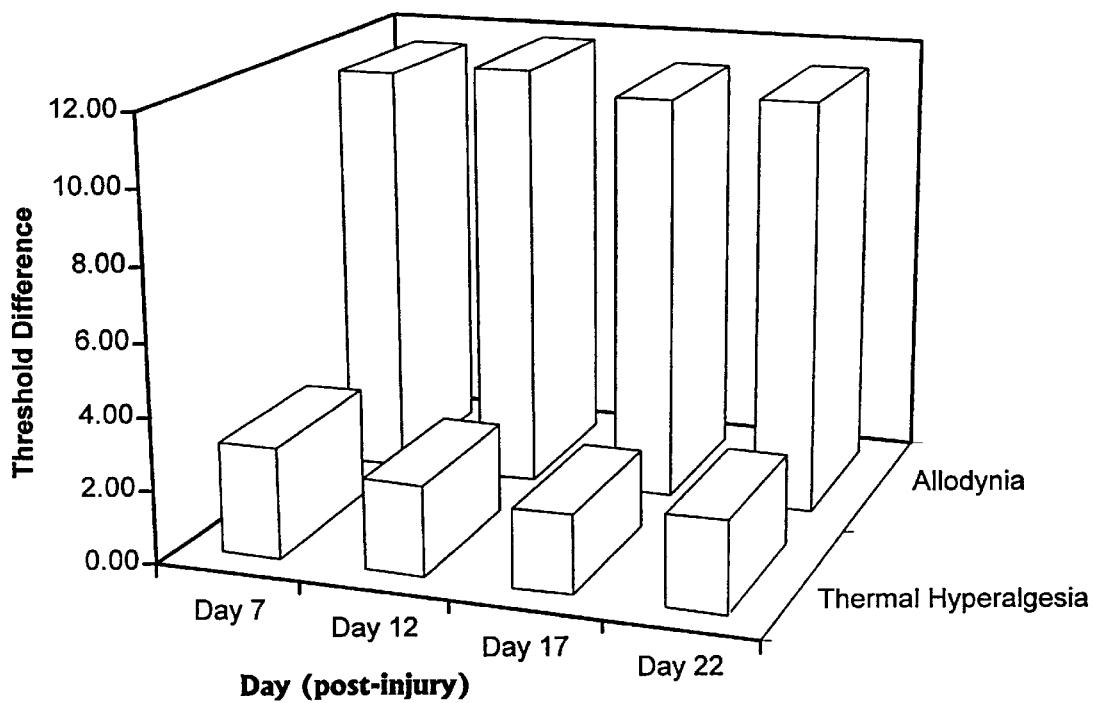
FIG. 1 is a graph illustrating the difference in the threshold pain response over 22 days in the ipsilateral and contralateral paws of rats subjected to nerve ligation. The row of bars at the back of the figure illustrates the static mechanical allodynia 50% withdrawal threshold (grams) of nerve-ligated rats, and the row of bars at the front of the figure illustrates the thermal hyperalgesia (seconds) on successive days following spinal nerve ligation. Values depict group means (n=6 per group).

In accordance with the present invention, a new method has been discovered for producing local analgesia by local administration of a tricyclic, second generation or third generation antidepressant to a body site of local discomfort.

Examples of tricyclic antidepressants useful in the practice of this invention are those having the structure:

wherein Z is a 7-membered ring, optionally containing 1 or 2 biocompatible heteroatoms, or an 8-membered bicyclic ring, Ar$_1$ and Ar$_2$ are optionally substituted aromatic rings fused to Z, and R is an alkylamino or arylamino substituent.

Examples of Z as an 8-membered bicyclic ring include (2,2,2,)bicyclooctane and (3,2,1) bicyclooctane, and the like. Oxygen and nitrogen are the preferred heteroatoms for optional inclusion in Z, the central ring of the three ring structure, but sulfur can also be included. R can be an alkylamino or arylamino substituent, or an N-oxide derivative thereof and generally comprises from 4 to 5 carbons, although as few as two carbons or as many as seven carbons, or even as many as 10 carbons can be contained in R. If R is an alkylamino substitutent, in some embodiments the alkylamino is a tertiary or secondary amino group. For example, R can be

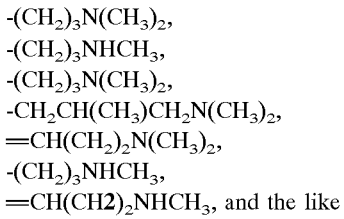

The preferred point of attachment of R to the tricyclic structure is at carbon 5, or to a heteroatom located at position 5 in the ring structure.

Examples of the optional biocompatible halogen substituent for Ar$_1$ and/or Ar$_2$ are chlorine, bromine and fluorine, with chlorine being preferred. For example Ar$_1$ and/or Ar$_2$ can be substituted with one or two of the biocompatible halogen atoms.

Non-limiting examples of tricyclic antidepressants useful in the practice of the present invention are clomipramine, imipramine, amitryptyline, desipramine, nortriptyline, amoxapine, maprotiline, trimipramine, and the like, and suitable combinations of any two or more thereof. Amitriptyline and desipramine are presently preferred.

Additional antidepressants contemplated for use herein include compounds sometimes referred to as "second-generation" or "third-generation" antidepressants, having pharmacokinetics and potency similar to those of the tricyclic antidepressants described herein. Examples of second generation or third generation antidepressants useful in the practice of the invention are those having the structure

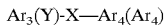

wherein Ar$_3$ is an N-containing heterocyclic ring, eg., a substituted 1,2,4-triazole or triazone, Y is either an aryl group fused to the heterocyclic ring or one or two substituents selected from alkyl, alkyloxy, arylalkyl, arylalkyloxy, aryl and heteroaryl substituents comprising a total of about 4 to 8 carbons attached to Ar$_3$, X is an alkyl group comprising 2 to 5 carbon atoms linking Ar$_3$ and Ar$_4$, Ar$_4$ is a piperazine attached to X by a first nitrogen atom of Ar$_4$, and Q is benzene ring optionally substituted with a biocompatible halogen, and attached to Q at a second nitrogen atom of Ar$_4$.

For example, X can contain 3 carbons, and Ar$_3$ can be a 1,2,4-triazone substituted at the 4 position with an arylalkyloxy substituent containing 6 to 8 carbon atoms. In an embodiment presently preferrred, Y is a heteroarylalkyl substituent containing an oxygen atom.

The preferred biocompatible halogen substituents for Q are selected from chlorine, bromine and fluorine.

Representative examples of second generation or third generation antidepressants useful in the practice of the present invention are trazodone, bupropion, mirtazapine, venlafaxine, fefazodone, and the like.

In one aspect, the present invention includes compositions for local administration of tricyclic, second generation or third generation antidepressants to a subject having a site of local discomfort. Such compositions are specifically formulated to ensure substantially local, rather than systemic administration of such antidepressant(s). In addition to one or more of the antidepressants described for use herein, the compositions of the invention may comprise one or more adjuvants which facilitate delivery, such as inert carriers, penetration enhancing agents, colloidal dispersion systems.

Representative and non-limiting examples of such inert carriers can be selected from water, isopropyl alcohol, gaseous fluorocarbons, ethyl alcohol, polyvinyl pyrrolidone, propylene glycol, a fragrance, a gel-producing material, stearyl alcohol, stearic acid, spermaceti, sorbitan monooleate, methylcellulose, and suitable combinations of two or more thereof.

The topical formulation can also include one or more known penetration enhancing agents selected to have minimal allergic or irritating effect. Known penetration enhancing agents include DMSO and azacyclo compounds, such as those disclosed in U.S. Pat. Nos. 4,755,535, 4,801,586, 4,808,414, an 4,920,101, which are incorporated herein, each in its entirety. No more of a penetration enhancing agent should be included in such compositions than is consistent with the goal of attaining substantially local delivery, rather than systemic delivery, of the tricyclic, second generation or third generation antidepressant(s). Those of skill in the art will be able to select a suitable penetration enhancing agent useful for the particular degree of penetration desired.

In another embodiment, the invention composition is formulated for local injection. In such an embodiment, the composition generally comprises a physiologically compatible saline solution and may optionally be encapsulated in a slow release delivery vehicle suitable for local injection, such as a colloidal dispersion system or in polymer stabilized crystals. Colloidal dispersion systems include nanocapsules, microspheres, beads, and lipid-based systems including oil-in-water emulsions, micelles, mixed micelles, and liposomes. The preferred colloidal system of this invention is a liposome or microsphere. Liposomes are artificial membrane vesicles which are useful as slow release delivery vehicles when injected or implanted, or when contained within a topical preparation. One type of microspheres suitable for encapsulating drugs for local injection is poly (D,L)lactide microspheres, as described in D. Fletcher, *Anesth. Analg.* 84:90–94, 1997.

The invention compositions may be formulated for topical administration, for instance as a cream, a lotion, a gel, an ointment, a spray, or an aerosol. Tricyclic, second generation and third generation antidepressants are quite lipid soluble themselves and, readily cross lipid barriers to gain access to central nervous system sites. This same property enables them to cross the perineurial barrier surrounding peripheral nerve endings (this barrier limits access of some agents to such sites, I. Antonijevic et al., Perineurial defect and peripheral opioid analgesia in inflammation, *J. Neurosci* 15 (1995) 165–172), giving them ready access to the peripheral nerve terminal and adjacent sites. Topical administration can also be effected by delivering the invention compositions via a slow release "patch." Therefore, in yet another embodiment, the composition further includes a patch delivery system having the antidepressant sequestered for slow release upon application to skin or mucous membrane.

In another aspect of the invention, there are provided methods for producing local analgesia in a subject, such as a mammal, by locally administering an effective amount of a tricyclic, second generation or third generation antidepressant(s) to a site of local discomfort. The term "local administration" includes any method of local administration known in the art. The antidepressant(s) used in the practice of the invention can be injected locally, for example, by subcutaneous or intra-articular injection. Alternatively, the tricyclic, second generation or third generation antidepressant(s) can be applied topically by applying a cream ointment, spray, or gel comprising the any antidepressant contemplated for use herein to an area of skin adjacent to a site of pain. Additional routes of local administration contemplated herein include topical application, local injection or subcutaneous implantation of the antidepressant encapsulated in a slow release vehicle, such as a liposome or microsphere.

The term "effective amount" means the quantity of a compound according to the invention necessary to prevent, to cure, or at least partially arrest a symptom of local pain or discomfort in a subject. A subject is any mammal, preferably a human. Amounts effective for creating a substantially local therapeutic effect will, of course, depend on the severity of the disease causing the painful condition, and the weight and general state of the subject. Typically, animal models, such as those described in the Background and Examples herein, may be used to determine suitable dosages to be used to achieve substantially local delivery of the tricyclic, second generation or third generation antidepressant(s). A recent pain scale developed by Galer et al. (Development and preliminary validation of a pain measure specific to neuropathic pain: The Neuropathic Pain Scale, Neurology 48 (1997) 332–338), which uses terminology specific for neuropathic pain, should be better able to delineate the symptoms within the syndrome. In addition, various general considerations taken into account in determining the "therapeutically effective amount" are known to those of skill in the art and are described, e.g., in Gilman et al., eds., *Goodman And Gilman's: The Pharmacological Bases of Therapeutics,* 8th ed., Pergamon Press, 1990; and *Remington's Pharmaceutical Science,* 17th ed., Mack Publishing Co., Easton, Pa., 1990, each of which is herein incorporated by reference.

The compositions and methods of the invention are particularly suited to producing local analgesia for painful symptoms known in the art as "neuropathic pain." As used herein the term "neuropathic pain" refers to pain syndromes known to be neuropathic (i.e., due to lesions or dysfunction in the nervous system) including certain relatively generalized syndromes, such as peripheral neuropathy, phantom pain, reflex sympathetic dystrophy, causalgia, central pain, syringomyelia, painful scar, and the like. Certain relatively localized syndromes are also considered to be neuropathic. Among these are specific neuralgias at any location of the body, head or face; diabetic, alcoholic, metabolic or inflammatory neuropathies; post herpetic neuralgias; post traumatic and post endodontic odontalgia; thoracic outlet syndrome; cervical, thoracic, or lumbar radiculopathies with nerve compression; cancer with nerve invasion; post traumatic avulsion injuries; post mastectomy pain, post thoracotomy pain; post spinal cord injury pain; post stroke pain; abdominal cutaneous nerve entrapments; primary tumors of neural tissues; and arachnoiditis, and the like.

Other pain syndromes believed to have a neuropathic component are stump pain, fibromyalgia, regional sprains or strains (crushing injury), myofascial pain, psoriatic arthropathy, polyarteritis nodosa, osteomyelitis, burns involving nerve damage, AIDS related pain syndromes, and connective tissue disorders, such as systemic lupus erythematosis, systemic sclerosis, polymyositis, and dermatomyositis, and the like.

The compositions and methods of the invention are also particularly suited to producing local analgesia for symptoms of localized pain and discomfort caused by inflammatory conditions. Inflammatory conditions that can be treated in the practice of the invention include conditions of acute inflammation (e.g. trauma, surgery and infection) or chronic inflammation (e.g., arthritis and gout).

The relative high concentrations of drugs attainable by local administration, coupled with a lesser incidence of the side effects characteristic of systemic absorption, produce particular benefits in treatment of discomfort associated with inflammatory or neuropathic pain conditions using the compositions and methods of this invention.

A rat spinal nerve ligation (SNL) model was used to determine the effect of tricyclic, second generation or third generation antidepressant(s) against neuropathic pain as described in full in the Examples herein. In this model, locally administered amitriptyline and desipramine, tricyclic antidepressants, were shown to be effective in alleviating thermal hyperalgesia. The local anti-hyperalgesic effects of amitriptyline and desipramine administered to a nerve-damaged hindpaw were observed without a concomitant analgesic effect on the contralateral paw. The maximal effect of locally administered amitriptyline was equal in magnitude to that of systemic injection, but alleviated manifestations of neuropathic pain over a longer time period than did systemic administration of the drug. This local effect produced no change in the thermal threshold of the contralateral paw or the paw of naive animals following local administration. Further, the local nature of this effect was verified when injections into the contralateral paw were found to have no significant effect on ipsilateral response latencies.

Figure 5A:
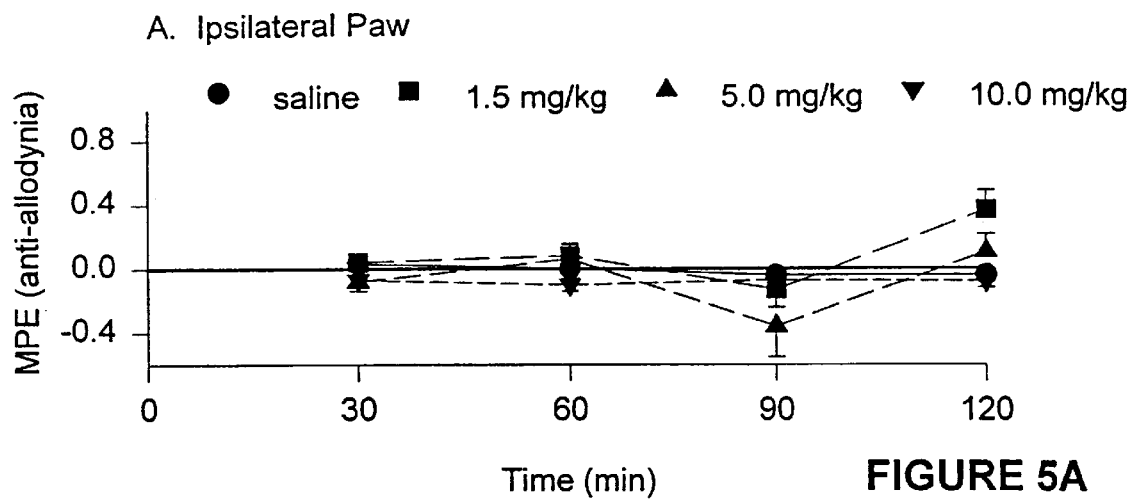
FIGS. 5A–C are a series of graphs illustrating the time course of the effect of systemic amitriptyline on static mechanical allodynia in the ipsilateral paw (FIG. 5A) and on the threshold of withdrawal to static mechanical stimuli in the contralateral paw (FIG. 5B), with ●=saline control; ■=1.5 mg/kg AMI; ▲=5 mg/kg AMI, and ▼=10 mg/kg AMI.
Figure 5B:
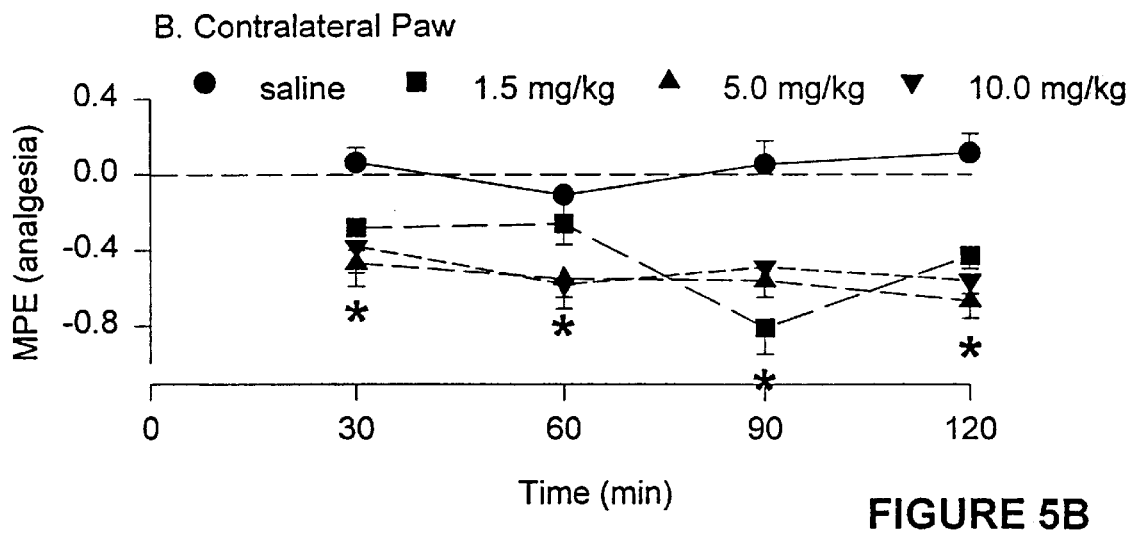
Figure 5C:
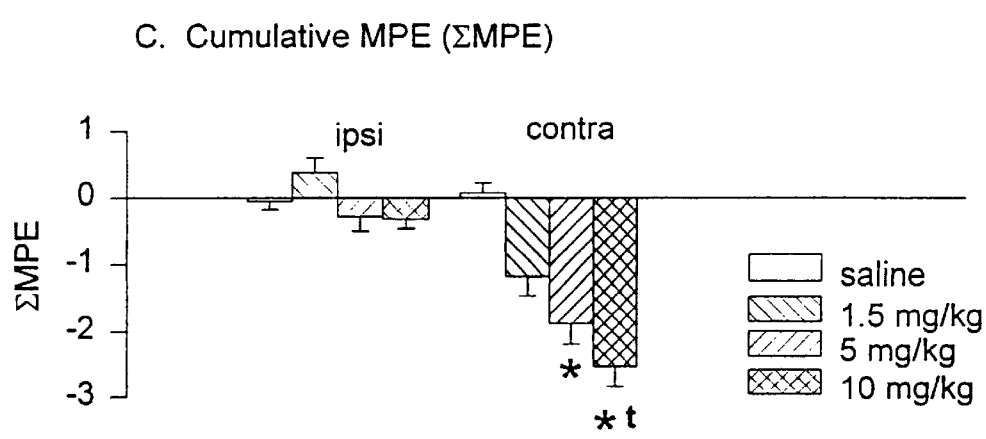
Figure 6A:
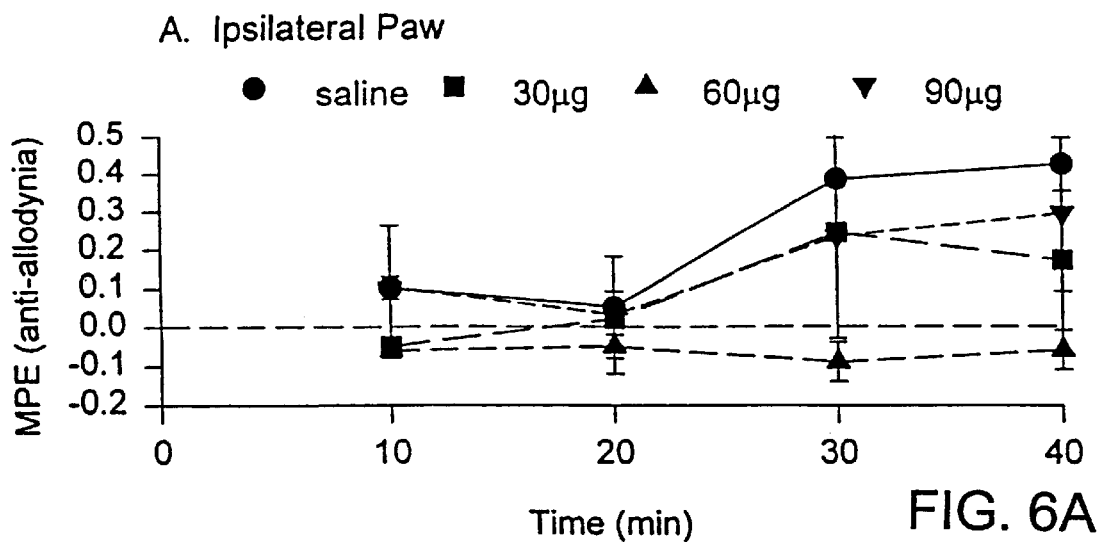
FIGS. 6A–C are a series of graphs illustrating the time course of the effect of spinal amitriptyline on static mechanical allodynia in the ipsilateral paw (FIG. 6A), on the threshold of withdrawal to static mechanical stimuli in the contralateral paw (FIG. 6B), with ●=saline control; ■=30 µg AMI, ▲=60 µg AMI, and ▼=90 µg AMI.
Figure 6B:
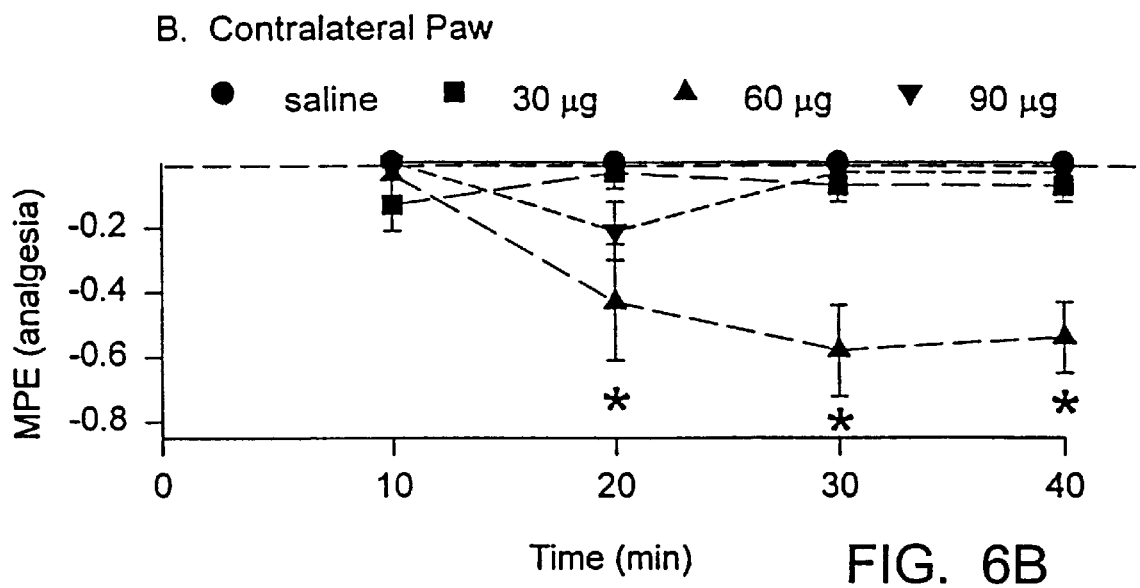
Figure 6C:
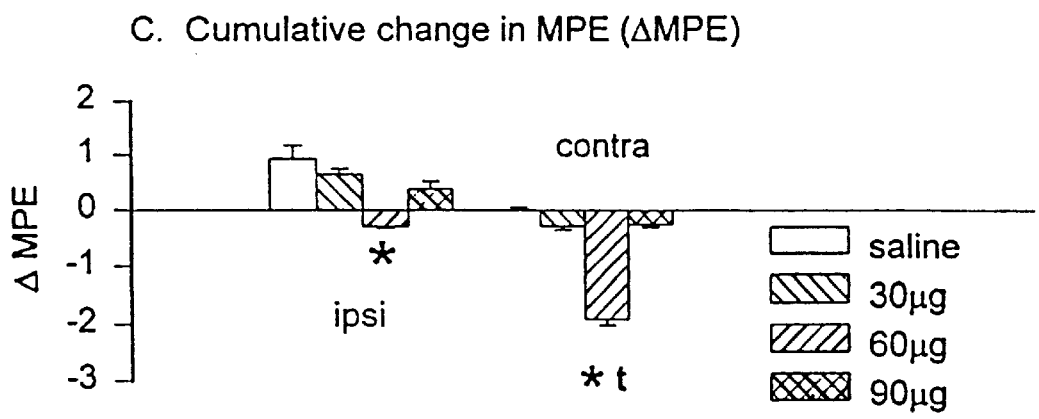

In contrast to the beneficial actions of locally administered amitriptyline against thermal hyperalgesia, amitriptyline was observed to be ineffective in the treatment of nerve injury-induced mechanical allodynia. There may even be a slight untoward effect following spinal administration of amitriptyline (60 μg) that became statistically significant when the cumulative change in the maximum possible effect (ΔMPE) was analyzed (FIG. 6C). Increasing the spinal dose of amitriptyline to 90 μg, however, caused a significant sedative effect so that the animals were flaccid in the testing apparatus, a result that hindered their ability to respond to the stimuli. An interesting observation with the use of amitriptyline in the allodynia test was the decrease in response threshold observed in the contralateral paw (FIGS. 5A–C, 6A–C, and FIGS. 7A–C), an effect referred to herein as a "hyperaesthetic tactile response." While the hyperaesthetic response threshold was similar to that of the nerve injured paw qualitatively, the observed behavioral response (a brisk withdrawal) differed from that exhibited by a normal neuropathic pain response (i.e., biting, licking, and guarding). The results of this study indicate that amitriptyline preferentially alleviates thermal hyperalgesia through all routes of administration, but has no effect on allodynia.

These findings suggest that the pathophysiology of thermal hyperalgesia and tactile allodynia are maintained through distinct mechanisms, which has also been suggested by the differential profile of other drugs like dextromethorphan on these two endpoints (M. Tal and G. J.Bennett (1994) *Neuroreport* 5:1438–1440). Therefore, the efficacy of tricyclic antidepressants, such as amitriptyline in a patient may be determined by which of the neuropathic symptoms is the most strongly expressed. For example, in a patient presenting with robust allodynic like symptoms, amitriptyline and antidepressants with similar activity may not make any perceived difference in the pain. However, if the dominant complaint is one that can be characterized as hyperalgesia, amitriptyline and drugs with similar activity may provide relief.

The experiments upon which this invention is based also demonstrate a local peripheral antinociceptive action for antidepressants, such as tricyclic, second generation and third generation antidepressants, against inflammation. In the rat formalin test, a well known animal model for inflammatory conditions, the antinociceptive action is shown by reduction in pain responses (both flinching behaviors and biting/licking time) caused by injection of formalin into a rat paw. The local nature of this action is verified in the animal model by the lack of effect of amitriptyline injected into the contralateral hindpaw. The antinociceptive effect is seen at locally injected doses of amitriptyline up to 100 nmol, which corresponds to a systemic dose of 0.22 mg/kg (for a 142 g rat). In the 2.5% formalin test, amitriptyline, desipramine and fluoxetine 10–300 nmol produced a dose-related reduction in phase 2 (16–60 min) flinching and in biting/licking behaviours when coadministered with the inflammatory irritant, formalin. Phase 1 flinch behaviours (0–12 min) were reduced at the highest dose. This action was locally mediated, as it was not seen when the antidepressants (100, 300 nmol) were injected into the contralateral hindpaw. The local action of desipramine and fluoxetine was partially altered by coadministration of caffeine 1500 nmol, but the action of amitriptyline was reversed by caffeine.

The peripheral action of amitriptyline involves an interaction with endogenous adenosine systems as shown by the Examples herein. A similar peripheral antinociceptive action of $NH_2dAD$, an inhibitor of adenosine kinase, which also acts by changing the extracellular availability of adenosine, is shown in the rat formalin test.

The local effect of locally administered tricyclic, second generation or third generation antidepressants as demonstrated in the formalin test is quite robust, with phase 1 and phase 2 flinching behaviors and the total biting/licking time being suppressed markedly.

While the mechanism of action of the antidepressants does not form a part of this invention, it has been determined that the peripheral antinociceptive action of amitriptyline involves endogenous adenosine with a subsequent activation of adenosine $A_1$ receptors on sensory nerve terminals (reviewed Sawynok J (1997) In: *Purinergic Approaches to Experimental Therapeutics* (Ed. Jacobsen K, Jarvis M) Wiley-Liss Inc, New York, 495) This observation is based on the ability of caffeine, a non-selective adenosine $A_1$ and $A_2$ receptor antagonist, and CPT, a selective adenosine $A_1$ receptor antagonist, to inhibit the action of amitriptyline on phase 2 flinching responses and biting/licking time. Phase 1 responses were unaffected by caffeine, and may result from another mechanism.

The studies upon which this invention is based also demonstrate that an inhibitor of adenosine kinase ($NH_2dAD$) can augment the local action of amitriptyline. Adenosine kinase is an intracellular enzyme (reviewed J. D.Geiger et al., Regulators of endogenous adenosine levels as therapeutic agents in: Purinergic approaches in *Experimental Therapeutics*, Ed. Jacobsen, K. A. and Jarvis, M. F, Wiley-Liss Inc., New York (1997 55–84) and its inhibition would result in an intracellular accumulation of adenosine and an efflux of adenosine from the cell along a concentration gradient This effect would enhance the extracellular adenosine available for uptake and the interaction with amitriptyline. Inhibition of adenosine deaminase with 2'-deoxycoformycin did not produce the same response, and this is generally consistent with the relative intrinsic effects expressed by these two agents.

It is important to note that in the experiments described herein all of these influences on adenosine availability are superimposed on an inflammatory stimulus (formalin). Endogenous adenosine is released peripherally by formalin (Doak G J, Sawynok J (1995) *Eur J Pharmacol* 281:311), as well as by inflammatory processes in general (Cronstein, 1994). Thus, the stimulus generates the substrate (adenosine and its uptake) with which amitriptyline interacts. The lack of, or more limited, effect of amitriptyline observed at lower concentrations of formalin inflammatory model (FIGS. 10A–C) may well be due to an inadequate release of endogenous adenosine at the lower stimulus intensity.

Similarly, the experiments on which this invention is based have shown that caffeine and CPT were without an intrinsic effect at 1.5% formalin, or slightly reduced the effect of formalin at 2.5% (cf. FIGS. 11A–C, 12A–B and 13A–B). The lack of effect of CPT indicates that the amount of endogenous adenosine generated by the formalin was insufficient to produce antinociception; such a response only occurred when amitriptyline was present and inhibited adenosine uptake. The modest effect of caffeine at 2.5% formalin may reflect a slight predominance of adenosine $A_2$ receptor activation in this experiment. Caffeine has been shown to lack a peripheral intrinsic effect due to blockade of opposing influences of adenosine $A_1$ and $A_2$ receptors (Doak G J, Sawynok J (1995, supra).

In the spinal nerve ligation model, amitriptyline (100 nmol) and desipramine (100 nmol), but not fluoxetine (100 nmol), produced a local and complete antihyperalgesic action in the hindpaw corresponding to the ligated side when thresholds were determined using a thermal paw stimulator. Desipramine and amitriptyline, at 100 and 300 nmol, which are maximally effective doses, produced a slight increase in paw volume, but fluoxetine produced a robust and sustained increase in paw volume over the complete dosage range (10–300 nmol). No agent significantly altered the degree of paw swelling produced by formalin in the inflammatory pain model when coinjected with the formalin. The increase in paw volume produced by fluoxetine was inhibited by ketanserin, a selective 5-$HT_2$ receptor antagonist, but not by other selective 5-HT receptor antagonists. The pronounced local pain alleviating actions in the absence of marked changes in paw volume produced by the tricyclic antidepressants desipramine and amitriptyline in the formalin test and the spinal nerve ligation model indicate that tricyclic, second generation or third generation antidepressant(s) can be used to produce local analgesia, for example in inflammatory and neuropathic pain states.

The invention will now be described in greater detail by reference to the following non-limiting examples.

EXAMPLE 1

Experiments were conducted on male Sprague-Dawley rats (100–120 gm) (Charles River, Quebec, Canada). Animals were housed in pairs, maintained on a 12:12 hour light-dark cycle at 22°∓1° C. and given ad-libitum access to food and water.

A. Preparation of the spinal nerve ligation animal model

Surgery on male rats was performed using aseptic technique under a dissection microscope and with adherence to the guidelines of the IASP on animal experimentation in pain research. The neuropathic condition was created by a tight ligation of the dorsal roots of lumbar nerves L-5 and L-6. Sprague Dawley rats (100–125 gm) were anaesthetized and surgically maintained using Halothane (1.5–2.0%). The animals were surgically clipped in the dorsal pelvic area. Antibacterial eye drops were applied to the eyes to prevent drying through the course of the surgical procedure. The animals were placed on a water heated pad (37∓0.5° C.). The area for surgical incision was cleansed and sterilized with ethyl alcohol and iodine. A 3 cm incision was made along the dorsal midline with the position of the iliac crest indicating the incision midline. A stab incision was made on the left side of the vertebral column at the level of the sacrum. The ligament attachments to the spinal cord were cut 2 cm rostral to the stab incision. Blunt dissection was used to further disconnect and separate the remaining tissue from the spinal cord. One retractor was placed at the L-4 vertebrae and a second retractor was used to counter retract the muscle away from the sacroiliac crest. Blunt dissection was used to clear the sacroiliac crest, the L-6/S-1 articular (facet) joint, and the transverse process of L-6. The facet was nipped off with rongeurs. A third retractor was used to retract the muscle away from the L-6 transverse process.

Under the dissecting microscope and using jewelers forceps, the connective tissue between the L-6 transverse process and the sacro-iliac rim was removed. Rongeurs were used to slowly nip away the transverse process of L-6 and expose the area for access to the L-5/L-6 nerve bundle. Using a glass probe the L-4/L-5 nerve bundle was hooked and manipulated to isolate the L-5 nerve. Once free of the L-4 nerve, the L-5 nerve was tightly ligated using 6-0 silk so that the nerve bulged on both sides of the ligature. The suture ends were trimmed and the nerve was allowed to fall back into its resting position. Again using the glass probe, the L-6 nerve was hooked from under the sacro-iliac rim, tightly ligated (6-0 silk), and placed back in position under the sacro-iliac rim. All damaged tissue was debrided, and all blood swabbed clear of the incision site. The muscle and tissue was gently rolled back into place to prevent any subdermal air pockets. The fascia over the muscle, and subsequently the skin was sutured shut (both using 3-0 Vicryl).

Post-operatively, the animals were placed in a recovery box with a heat lamp for observation. Following a successful surgery, the animals were fully ambulatory with no indications of spontaneous pain (licking, biting, or autonomy of the neuropathic foot, or vocalizations). If the animals presented initially with a foot drop of the neuropathic paw, that disappeared within 1–2 days post-operatively. Any animals that presented with locomotor deficits or symptoms of spontaneous pain 2 days post-operatively, were promptly euthanised with an overdose of halothane.

B. Behavioral Testing

All behavioral tests were conducted between 08:00 and 14:00 daily, and occurred at 7,12, 17, and 22 days following nerve injury. An exception to this was the cannulated animals, which were tested at 7 and 12 days after cannulation (14 and 19 days after nerve injury respectively). Following a recovery period of 7 days, animals were moved from the vivarium, weighed, and acclimatized to the testing room for 40 minutes. After this initial period the animals were placed in the testing apparatus for 30–40 minutes or until exploratory behavior ceased.

B.1. Establishment and maintenance of neuropathic pain for the testing periods

To determine that peripheral mononeuropathy resulted from ligation of L5 and L6 spinal nerves tests of static mechanical allodynia and thermal hyperalgesia were conducted.

B.2. Testing for Thermal Hyperalgesia

Surgically induced thermal hyperalgesia was assessed using a Paw Thermal Stimulator System. The animals were allowed two acclimatization periods prior to the testing (30 minutes post removal from housing facility; 20 minutes in individual testing chambers). Rats were placed in pairs in a plexiglass box on top of the temperature maintained glass surface (30∓0.1° C.) of the stimulator. After the initial acclimatization period, rats were tested for baseline withdrawal latencies (seconds) of both paws once every 20 minutes until three stable baselines were achieved. The animals were then returned to their cages for 30–40 minutes prior to drug administration and given ad-libitum access to food and water. Following drug administration, the animals were returned to the testing boxes for testing.

B.3. Static Mechanical Allodynia

Following weighing and testing room acclimatization, rats were placed in an elevated plexiglass container with a wire mesh bottom to allow access to the ventral surface of the hind paws. Rats were further acclimated to the testing chambers and tested for experimental baseline (two tests in one hour) using Semmes-Weinstein monofilaments (Stoelting Comp., Wood Dale Ill.). The 50% withdrawal threshold was determined using the Dixons up-down method (Chaplan et al., 1994). Briefly, filaments were applied to the ventral surface of the paw starting with the 4.31 filament (2.04 gm) and the response noted. Following a positive response (paw withdrawal, with characteristic pain behavior), a lower filament was then applied. If no response was shown, the weight of the subsequent filament applied was increased. The 50% withdrawal threshold was then determined from the tabular value for the pattern of responses (k), the final monofilament value ($X_f$, in log units), and interpolated using the formula:

$$50\% \text{ g threshold} = (10^{[X_f + k\delta]})/10{,}000$$

where $\delta$ is the mean difference between stimuli. Following the determination of baseline values, the rats were returned to their original cages and left undisturbed with ad-libitum access to food and water for 30–40 minutes. After drug administration, the animals were again placed in the testing chambers and monitored for the appropriate behavioral periods depending on the route of drug administration. The results of these tests are shown in FIG. 1.

B.4. Data Analysis

For each of the experiments, raw data for response thresholds of both paws in each animal were recorded and entered into a spreadsheet (Microsoft Excel 5.0). The data was then normalized for each animal as Maximum Possible Effect (MPE) in terms of reversal of the neuropathic symptom being tested [MPE (anti-hyperalgesia or antiallodynia)] or in terms of the analgesic effect of the contralateral paw [MPE (analgesia)]. These values were calculated as follows:

MPE (anti-neuropathic)=(PDR–IBR)/(CBR–IBR), wherein PDR is the post drug response of the ipsilateral paw, IBR is the ipsilateral paw baseline response, and CBR is the contralateral paw baseline response. Similarly, the MPE (analgesia) was calculated as follows:

MPE (analgesic)=(PDR–CBR)/(cutoff–CBR), wherein cutoff was 20 seconds from the thermal stimulus and 15 g for tactile allodynia, and PDR is the post drug withdrawal threshold of the contralateral paw. Accordingly, the individual values reported or depicted are the MPE∓SEM. The time course of the drug effect is also depicted as the cumulative change in the MPE ($\Delta$MPE) for each treatment and route of administration. This value was calculated as the sum of the individual MPE values through the time course ($\Sigma_n$), assuming an MPE value of 0 for the baseline values (not shown in figures). The data was statistically analyzed using a one way ANOVA for repeated measures with a pairwise comparison (Dunnetts post hoc analysis). To compare the $\Delta$MPE values of multiple treatment groups a one-way ANOVA with a pairwise comparison (Student-Neuman-Keuls post hoc analysis) was used. When comparing the means at individual time points or in the $\Delta$MPE values, a student's T-test was used with a Student-Neuman-Keuls post hoc correction. For all tests, a P value less than 0.05 (P<0.05) was considered significant.

These tests showed that spinal ligation resulted in neuropathic pain in rats with presenting symptoms of static mechanical allodynia and thermal hyperalgesia, and the condition was maintained throughout the testing periods (days 7, 12, 17, 22). As shown by the data summarized in FIG. 1, the threshold values for thermal hyperalgesia were 7.98∓0.48 sec for the ipsilateral paw as compared to 10.35∓0.63 sec for the contralateral paw. Allodynia was manifested as 50% withdrawal threshold of 2.20∓0.28 g for the ipsilateral paw and 13.37∓0.37 g for the contralateral paw. Threshold values remained relatively stable with no statistically significant difference in baseline values for either the ipsilateral or the contralateral paw on each of the subsequent testing days.

B5. Drug Treatment

Tests were conducted to determine the antinociceptive effect of the tricyclic antidepressant amitriptyline in the ligated rat model. All drugs treatments were blinded. In both of the behavioral tests, amitriptyline (Sigma Chemical Co., St. Louis, Mo.) or saline was administered either systemically (by intraperitoneal (i.p.) injection), spinally (through an implanted intrathecal cannulas (i.t.)), or locally (by subcutaneous injection (s.c.) in the dorsal surface of the paw). Drugs were injected in volume of 5 ml/kg for systemic injections, and a total volume of 20 $\mu$l (10 $\mu$l drug+10 $\mu$l saline flush) for intrathecal injections. For local injections, the animals were briefly anaesthetized with halothane, and the solution was administered s.c. to the dorsal surface of the ipsilateral or contralateral paw in a volume of 50 $\mu$l.

Figure 2A:
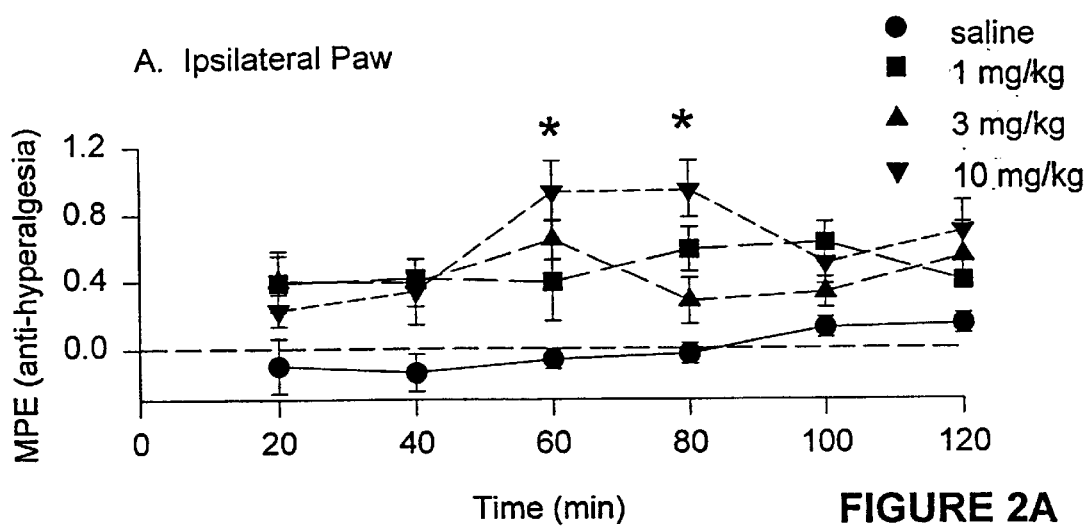
FIGS. 2A–C are a series of graphs illustrating the time course of the effect of systemic amitriptyline (AMI) at various doses on thermal hyperalgesia in the ipsilateral paw of nerve-ligated rats (FIG. 2A), and the thermal withdrawal threshold in the contralateral paw (FIG. 2B), with ●=saline control; ■=1 mg/kg AMIT; ▲=3 mg/kg AMI, and ▼=10 mg/kg AMI.
Figure 2B:
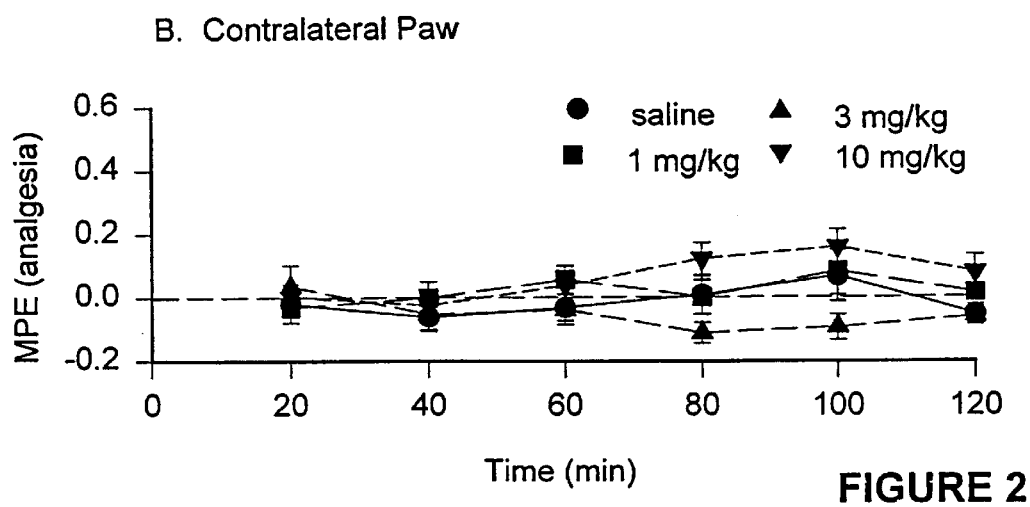
Figure 2C:
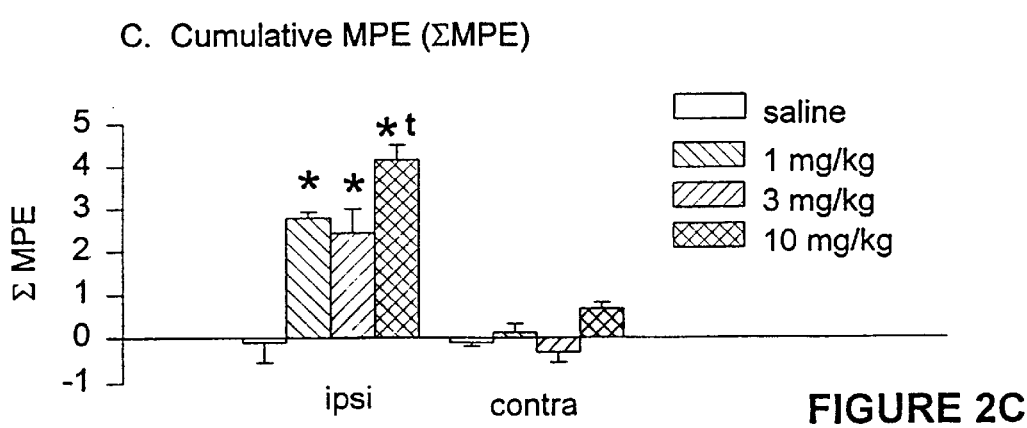

C1. Effect of systemic amitriptyline on nerve injury-induced thermal hyperalgesia Systemic administration to nerve-injured rats of amitriptyline at doses of 1, 3 and 10 mg/kg of body weight by ip. injection produced an anti-hyperalgesic effect on the thermal threshold of the nerve-injured paw, as shown by the data summarized on FIGS. 2A–C. This effect was maximal at 10 mg/kg; reaching an almost complete reversal of thermal hyperalgesia (MPE=0.94∓–0.17) 60–80 minutes after injection (FIG. 2A). A slight but not statistically significant elevation in threshold was observed in the contralateral paw for the 10 mg/kg dose (FIG. 2B). Comparison of the $\Delta$MPE values for the ipsilateral paw (FIG. 2C), shows a statistically significant antinociceptive effect of 10 mg/kg for amitriptyline as compared to saline controls, as well as for 1 mg/kg and 3 mg/kg doses. While both 1 mg/kg and 3 mg/kg doses produced results significantly different from those of the saline controls, they were not significantly different from each other. A slight sedative effect of the 10 mg/kg dose was observed in a few of the rats, but none was observed at other doses. This effect did not impact the ability of the animals to respond to the stimulus, as the vigor of the response at threshold was similar to that observed during baseline determinations.

C2. Intrathecal Cannulations

In animals used to study the effects of spinal administration of amitriptyline, intrathecal cannulas were implanted 7 days following nerve injury. For the implantation of intrathecal cannulas for the spinal delivery of drugs, rats were anaesthetized with halothane and mounted in the earbars of a stereotaxic apparatus. The cisternal membrane at the base of the skull was exposed, a small incision made, and a cannula (7.5 cm of PE-10 tubing) inserted into the subarachnoid space. The cannula was filled with saline and the external end was occluded with a small wire plug. Rats were injected with Penlong XL$^R$ (0.15 ml i.m.) and lactated Ringers solution (10 ml s.c.) while still anaesthetized. On the day of testing, rats were accommodated in a plastic container for the intrathecal injection (in a 10 $\mu$l volume followed by 10 $\mu$l saline to flush the cannula).

C3. Effect of spinal amitriptyline on nerve-injury induced thermal hyperalgesia

Figure 3A:
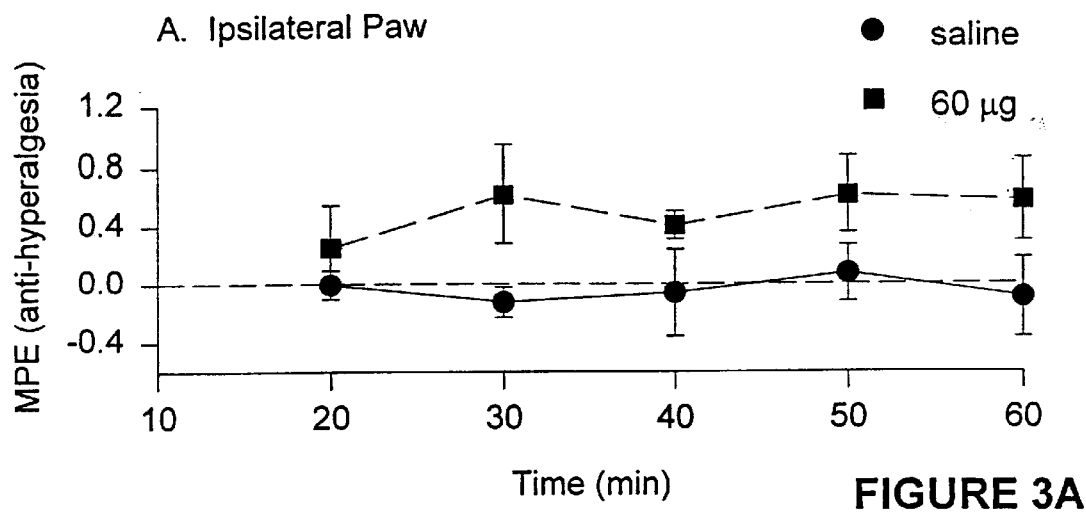
FIGS. 3A–C are a series of graphs illustrating the time course of the effect of spinal amitriptyline (60 µg) on thermal hyperalgesia in the ipsilateral paw (FIG. 3A), and the thermal withdrawal threshold in the contralateral paw (FIG. 3B), with ●=saline control, ■=60 µg AMIT.
Figure 3B:
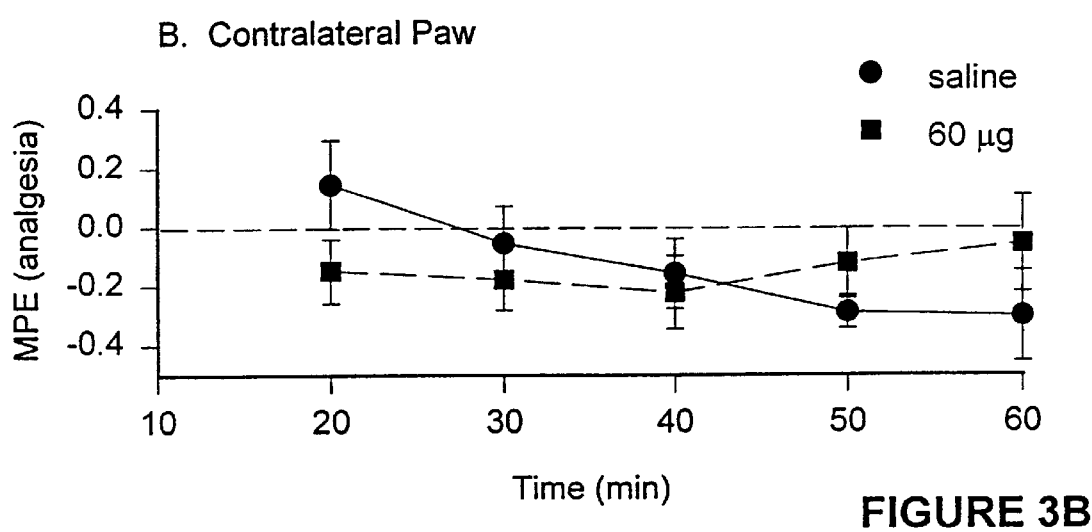
Figure 3C:
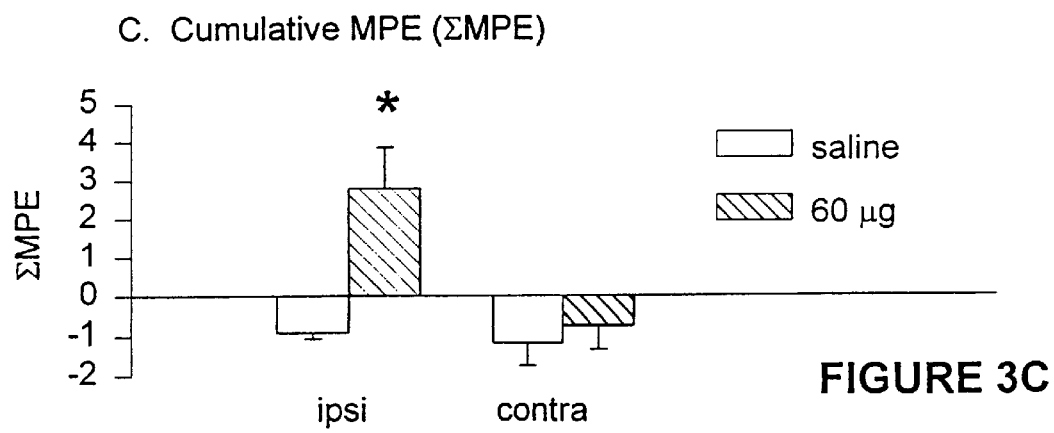

The intrathecal injection of amitriptyline (60 $\mu$g) resulted in a partial reversal of the thermal hyperalgesia of the ipsilateral paw in nerve injured rats that was evident 20 minutes after injection and lasted for the 60 minute testing period, as shown by the data in FIGS. 3A–C. Because a 30 $\mu$g dose was ineffective in the allodynia test, and 90 $\mu$g was highly sedative, these doses were not used for testing of the thermal hyperalgesic effect. While values for the individual time point are not significantly different on their own (FIG. 3A), the $\Delta$MPE values for saline and amitriptyline (60 $\mu$g)

were significantly different (FIG. 3C). No significant difference was observed, in the contralateral paw withdrawal thresholds, at either single time points or in comparison of the ΔMPE values (FIGS. 3B and 3C).

Figure 4A:
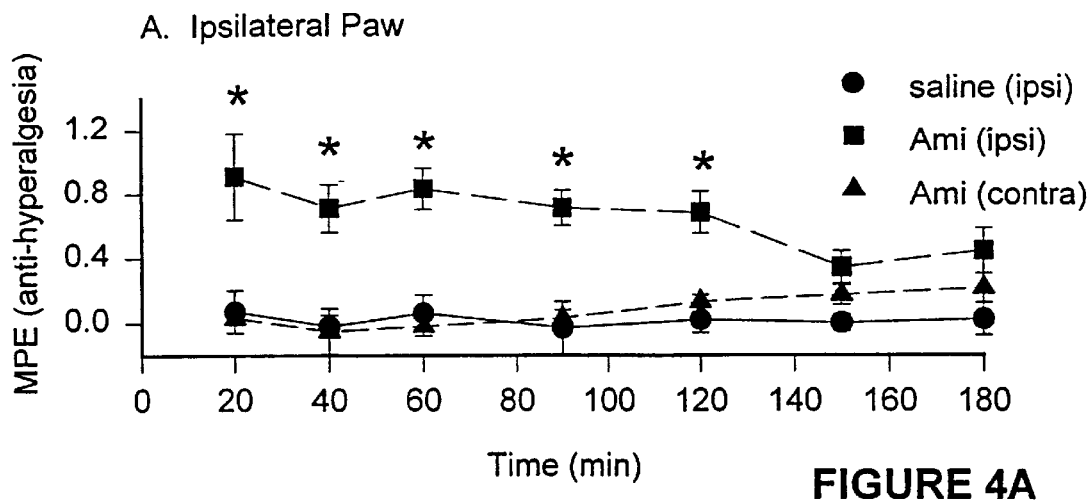
FIGS. 4A–C are a series of graphs illustrating the time course of the effect of local injection of 100 nmol amitriptyline on thermal hyperalgesia.
Figure 8A:
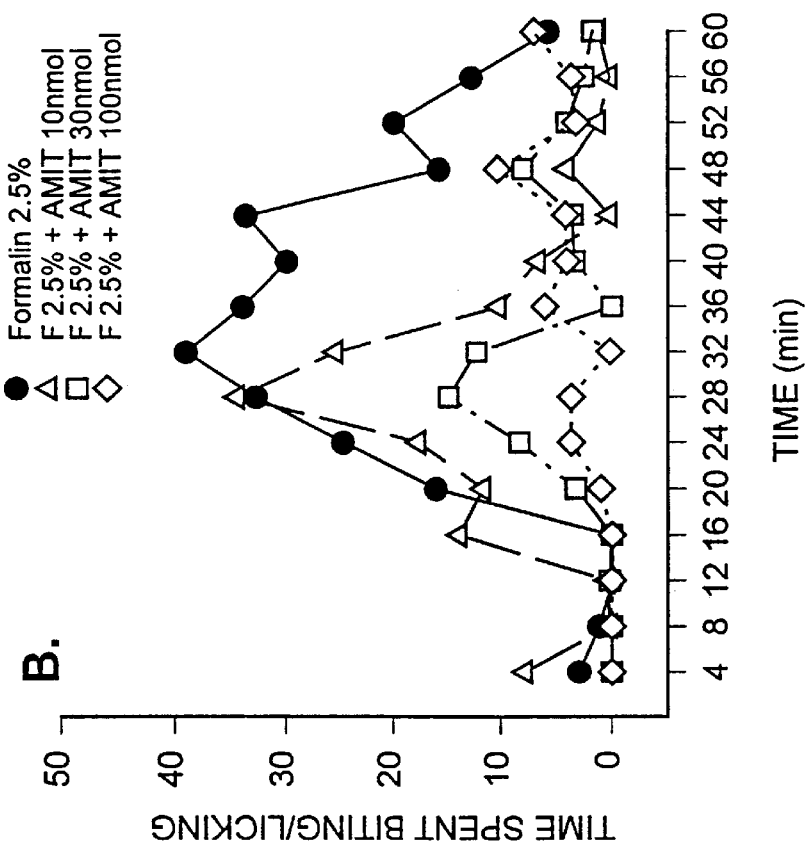
FIGS. 8A–B are two graphs illustrating the time course of the local antinociceptive effect produced by coadministration to rats of amitriptyline (AMI) with formalin 2.5% as measured by number of flinches (FIG. 8A) or time spent biting or licking (FIG. 8B). ●=2.5% formalin alone; open triangle=2.5% formalin+10 nM AMI; open square=2.5% formalin+30 nmol AMI; open diamond=2.5% formalin+100 nmol AMI. Values depict group means (n=5–11 per group); error bars for s.e.m. were omitted in the interest of clarity.

C4. Effect of local injection of amitriptyline on nerve injury-induced thermal hyperalgesia When injected locally into the neuropathic paw, amitriptyline at a dose of 100 nmol, which produces a local antinociceptive effect in the rat formalin test as described in Example 2 herein (FIG. 8), had an immediate statistically significant antinociceptive effect, almost completely reversing the thermal hyperalgesia in nerve-injured rats (FIG. 4A). The MPE values remained significantly different from those of saline for the first 120 minutes. A contralateral local injection of amitriptyline (100 nmol) failed to show any significant effect on the withdrawal latency of the ipsilateral paw (FIG. 4A), a result that indicates a lack of systemic effect. No local effect of the injected paw was observed either for the control rats injected with saline (ipsilateral paw) or for animals injected with amitriptyline (100 nmol) in the contralateral paw.

Figure 4B:
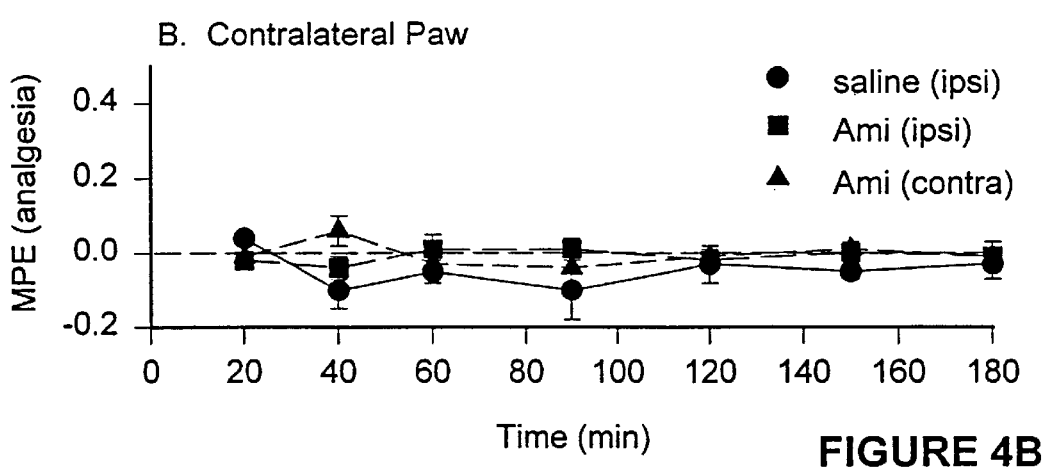
Figure 4C:
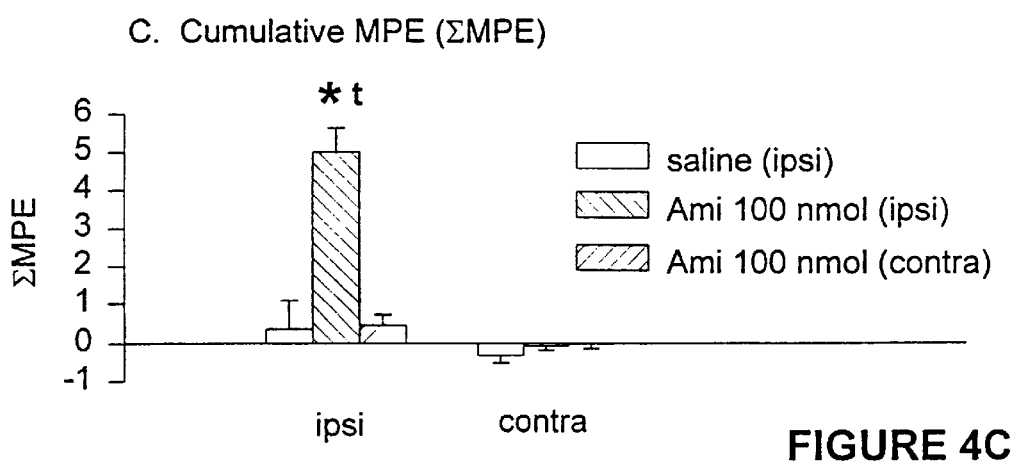

There was also no significant alteration in the withdrawal thresholds of naive animals after local injection of amitriptyline 100 nmol (n=4; data not shown). In addition, neither the ipsilateral nor contralateral local injections showed any significant effect on the contralateral paw withdrawal latency (FIG. 4B). Comparison of the ΔMPE values revealed a statistically significant difference resulting from locally injected amitriptyline on thermal hyperalgesia as compared to both the saline control and the contralateral injection control (FIG. 4C).

C5. Effect of systemic amitriptyline on nerve injury-induced mechanical allodynia Amitriptyline was systemically administered to nerve injured rats at doses of 1.5, 5.0, and 10.0 mg/kg of body weight. No significant effect on nerve injury induced allodynia in the ipsilateral paw was observed at any of the doses (FIG. 5A). Since 10 mg/kg was slightly sedative in some rats, a higher dose was not used. In the contralateral paw, all doses of amitriptyline caused a hyperaesthetic response resulting in a reduced MPE (analgesia) value ranging from −0.4 to −0.8 (FIG. 5B). The ΔMPE values for each dose differed significantly from saline (FIG. 5C). Qualitatively, the hyperaesthetic response was observed as a brisk withdrawal to the filament with no overt signs of typical neuropathic pain responses such as biting, licking, vocalization or guarding of the paw. Although the values of the response threshold in the non-injured paws were very similar to those in the injured paws, the responses were not categorized as 'neuropathic pain responses'. Threshold testing 24 hours after drug administration showed that both the ipsilateral and contralateral baselines returned to predrug values (data not shown).

C6. Effect of spinal amitriptyline on nerve injury-induced mechanical allodynia

Amitriptyline was also administered spinally to test its antinociceptive effect against nerve injury-induced mechanical allodynia in the ipsilateral paw, At doses of 30, 60, and 90 μg administered spinally, amitriptyline failed to have a significant effect on allodynia in the ipsilateral paw (FIGS. 5A and 6C). However a comparison of the ΔMPE for the three groups revealed the 60 μg group to be significantly different from the 30 μg and 90 μg groups, as well as from the saline group (FIG. 6C). Spinally administered amitriptyline (60 μg) caused a hyperaesthetic response in the contralateral paw (FIGS. 6B and 6C) that was similar in magnitude to that observed following systemic administration. While 90 μg dose (n=3) appeared not to facilitate the hyperaesthetic response, this result was probably due largely to the pronounced sedative effect of the drug at this dose, which interfered with accurate determination of the withdrawal threshold.

C7. Effect of local amitriptyline on nerve-injury-induced mechanical allodynia

Figure 7A:
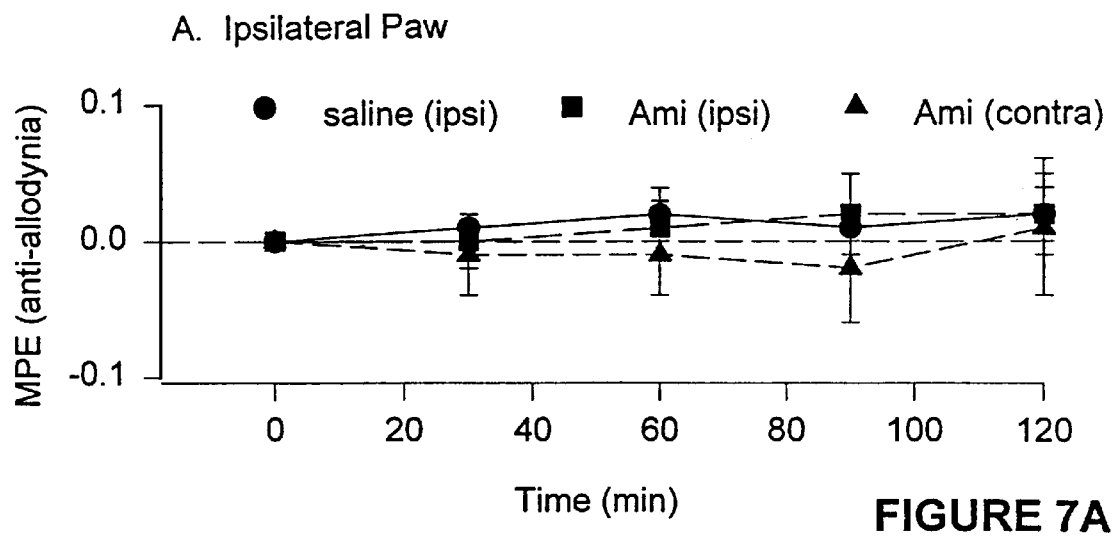
FIGS. 7A–C are a series of graphs illustrating the time course of the effect of local peripheral injection of amitriptyline (100 nmol) on mechanical allodynia.
Figure 7B:
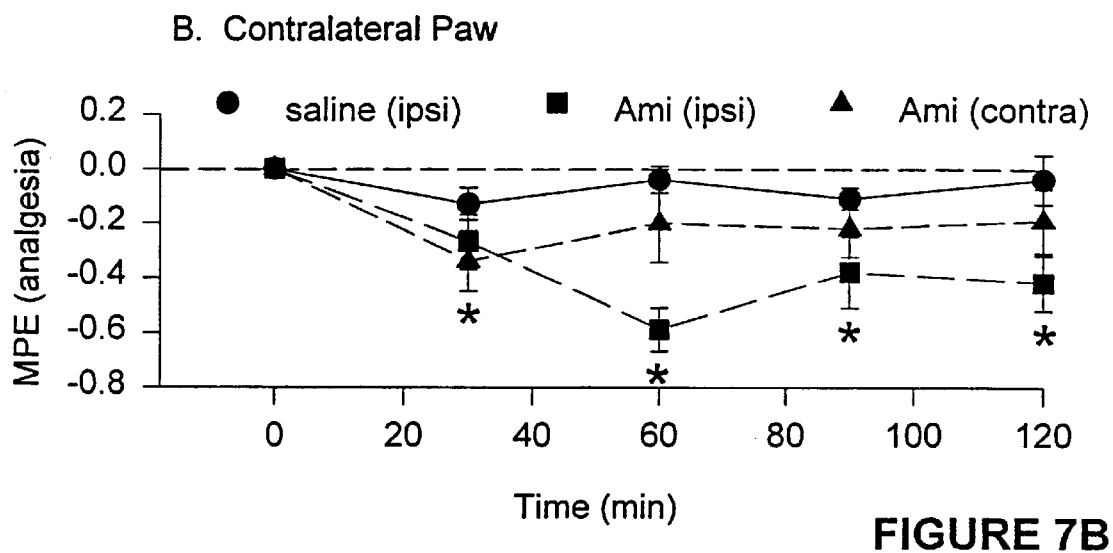
Figure 7C:
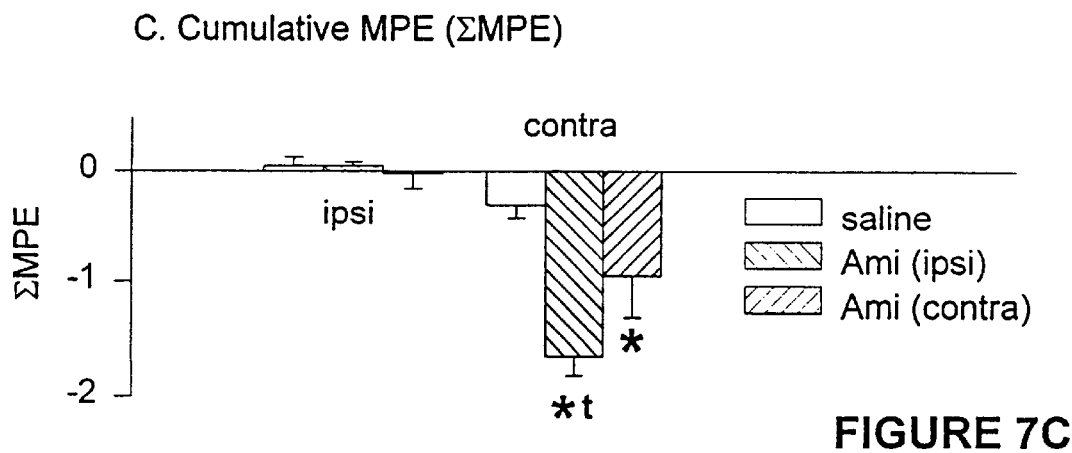

Amitriptyline was also injected locally to test the local effect on nerve-injury induced mechanical allodynia. Local injection of amitriptyline (100 nmol) failed to show any significant effect on the withdrawal response of the nerve injured paw to tactile stimulation (FIGS. 7A and 7C). Local injection of amitriptyline into the nerve injured paw did, however, cause a reduction in the response threshold of the contralateral paw. This effect also occurred after direct local injection of amitriptyline (100 nmol) into the non-injured contralateral paw (FIG. 7B). The response to locally administered drug in the contralateral paw was observed to be significantly different from the response to saline, but not different from the response following injection into the non-injured paw at individual time points (FIG. 7B) and in comparison of the ΔMPEs (FIG. 7C).

EXAMPLE 2

Experiments were performed using male Sprague-Dawley rats (120–160 g; group mean 142∓4 g) (Charles River, Quebec, Canada). Rats were housed in pairs and maintained on a 12:12 h light/dark cycle at 22°∓1° C. Food and water were freely available.

The test drugs were amitriptyline, caffeine, 5'-amino-5'-deoxyadenosine ($NH_2dAD$), phentolamine HCl, dimethylsulfoxide (DMSO) (Sigma Chemical Co., St. Louis, Mo.), 8-cyclopentyl-1,3-dimethylxanthine (CPT), $N^6$-benzyl-N-ethylcarboxamide adenosine ($N^6$-benzyl-NECA), MK-801 hydrogen maleate, naloxone HCl (Research Biochemicals Inc., Natick, N.J.), 2'-Deoxycoformycin (Parke Davis Pharmaceutical Research Division, Ann Arbor, Mich.). Formalin (37% formaldehyde) (British Drug Houses, Toronto, Ontario) was the control irritant. All drugs except for CPT were dissolved in saline and diluted to the appropriate dose with formalin. CPT was dissolved in a final concentration of 15% DMSO, and appropriate control groups were included.

A. The Formalin Test

On the day of testing, rats were placed in a 28×28×28 cm plexiglass observation chamber for an initial 20 min to allow familiarization with surroundings. The indicated doses of formalin (0.5–2.5%) and formalin/drug combinations were injected s.c. in a volume of 50 μl into the dorsal hindpaw of the rat. To establish whether inhibition of pain response was due to a systemic rather than a local effect, the test drug was administered into the contralateral paw. For injections into the contralateral paw, the drug was injected immediately before the formalin in the other paw. Following injections, rats were returned to the observation chamber, and flinching behaviors (lifting, shaking or rippling of the haunch) were monitored over two time periods, phase 1 (0–12 minutes following administration) and phase 2 (16–60 minutes following administration). Biting/licking time was also monitored. Flinches, which were rapid events, were recorded as discrete episodes, while the time spent biting or licking was recorded cumulatively. Two rats in adjacent chambers were observed at a time, with observations taking place in alternating 2 min bits. Recorded episodes and times were not corrected, with the result that values obtained represent about half of the total behaviors expressed.

Data was analyzed using analysis of variance followed by the Student-Neuman-Keuls test for multiple groups, or the Student t-test for two groups.

B. Local Antinociceptive Action of Amitriptyline

Figure 8B:
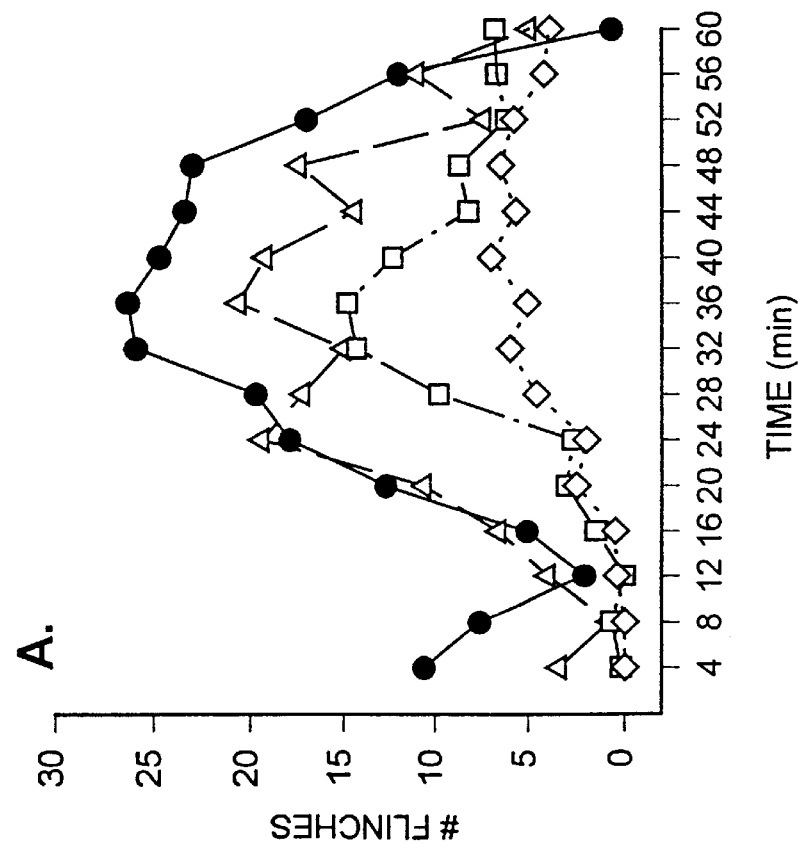
Figure 9A:
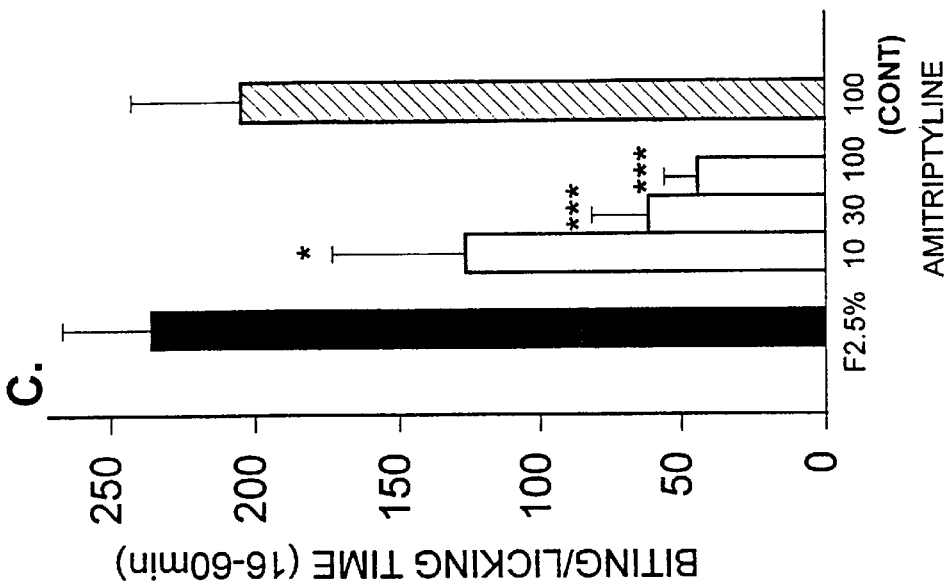
FIGS. 9A–C are a series of bar graphs illustrating the cumulative scores for phase 1 flinches (FIG. 2A), phase 2 flinches (FIG. 9B), and biting/licking time (FIG. 9C) following coadministration to rats of amitriptyline (100 nmol) with 2.5% formalin (F). The antinociceptive effect of amitriptyline administered to the ipsilateral paw (local effect) was not reproduced by administration of amitriptyline into the contralateral (CONT) hindpaw. The values depicted are∓s.e.m. values (n=5–11). *=P<0.05, =P<0.01, and *=P<0.001 compared to the formalin alone group.
Figure 9B:
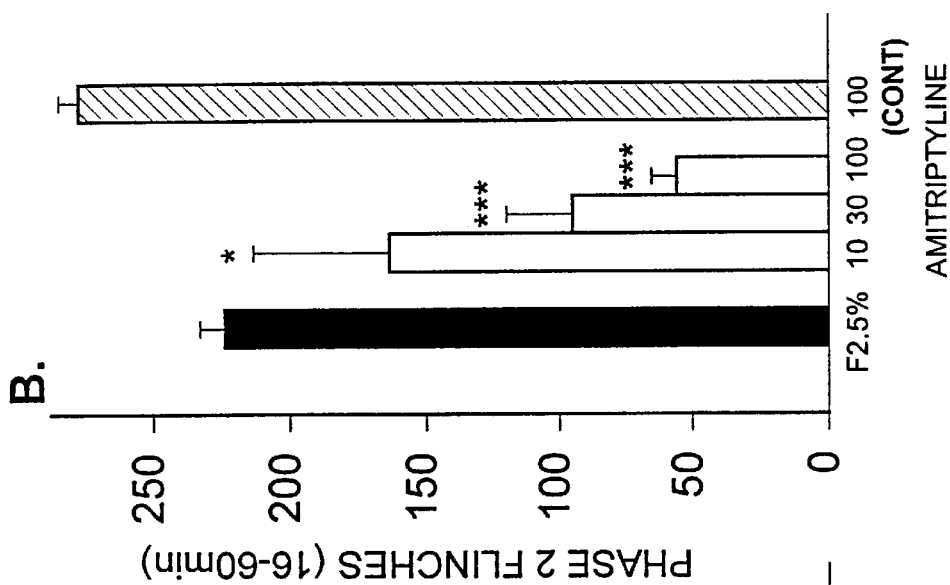
Figure 9C:
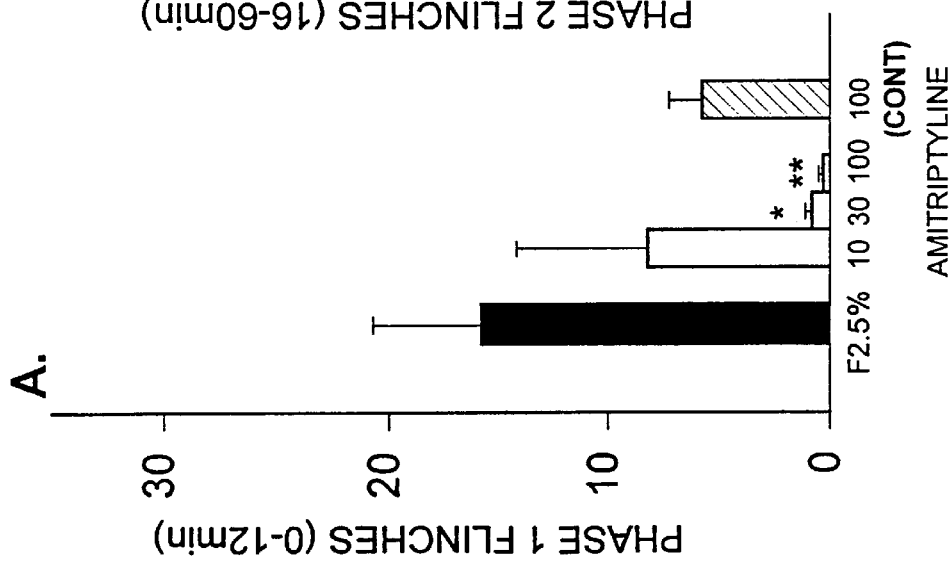

To test the antinociceptive effect of locally administered antidepressant, amitriptyline was coadministered at doses of 10, 30, and 100 nmol with 2.5% formalin. A dose-dependent reduction in the expression of flinching behaviors both in phase 1 and phase 2 following injection was observed. The time course for these effects is presented in FIG. 8A, and the cumulative scores for the two phases are presented in FIGS. 9A and 9B. A similar dose-related inhibition in biting/licking behaviors was obtained (FIGS. 8B and 9C); however, there was no distinct phase 1 effect observed in biting/licking behaviors (FIG. 8B). The inhibitory effect of amitriptyline on both parameters was not observed following administration of amitriptyline into the contralateral hindpaw (FIGS. 9A–B). The absence of inhibitory effect on the contralateral hindpaw indicates that the antinociceptive action of amitriptyline is a local effect.

Inhibition of pain was seen most clearly at higher concentrations of formalin. For example at 0.75% formalin, the effect was seen only with flinching behaviors, while at 0.5%, it was not seen at all (FIG. 3).

Figures 11A, 11B, 11C:
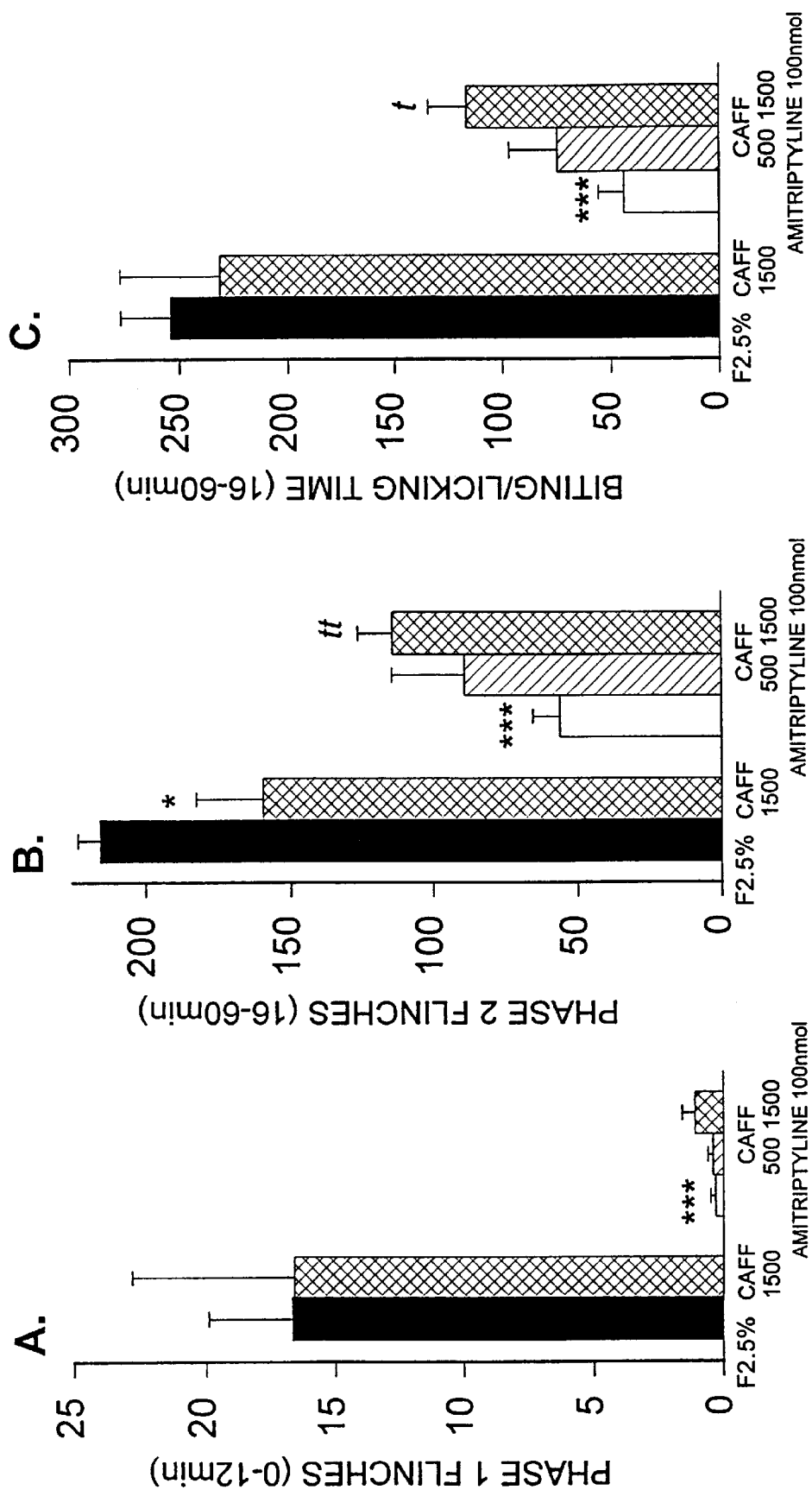
FIGS. 11A–C are a series of graphs illustrating partial reversal of the local antinociceptive action of amitriptyline in the 2.5% formalin (F) test by coadministration with caffeine (CAFF) as measured by phase 1 flinches (FIG. 11A), phase 2 flinches (FIG. 11B), and time spent licking and biting (FIG. 11C). n=10–15 except for the caffeine (1500 nmol) group where n=5. *=P<0.05, ***=P<0.001 compared to the formalin only group; t=P<0.05, tt=P<0.01 compared to formalin/amitriptyline group. The filled bars illustrate 2.5% formalin alone, the empty bars illustrate administration of AMI alone, the bars with leftward sloping lines illustrate AMI+500 nmol CAFF, and the crosshatched bars illustrate 1500 nmol caffeine alone or with 100 nmol AMI.

C. Involvement of Adenosine in the Local Antinociceptive Action of Amitriptyline To examine involvement of adenosine in the antinociceptive action of amitriptyline, caffeine, a non-selective adenosine antagonist, was coadministered at doses of 500 and 1500 nmol with amitriptyline. A significant reversal of the antinociceptive action of amitriptyline was observed in phase 2 flinches and total biting/licking time, but phase 1 flinches were not affected (FIGS. 11A–C). Although there was only a partial reversal of amitriptyline action at 2.5% formalin caused by caffeine, caffeine clearly reversed the local effects of adenosine. Therefore, it was speculated that the expression of adenosine may depend on the intensity of the pain stimulant. To test this hypothesis, some experiments were undertaken using a lower concentration of formalin. Amitriptyline at 100 nmol concentration reduced phase 2 flinches to formalin 1.5% to a lesser extent than in the 2.5% formalin test, but caffeine produced a complete reversal of the antinociceptive action of amitriptyline (FIG. 13A). However, at a higher dose of amitriptyline (300 nmol), which produced a comparable extent of inhibition as did 100 nmol with 2.5% formalin, the degree of reversal by caffeine was still only partial (FIG. 13A).

CPT, a selective adenosine $A_1$ receptor antagonist, coadministered at a dose of 150 nmol with 100 nmol amitriptyline produced a similar degree of reversal of the action of amitriptyline as did caffeine in the 1.5% formalin test (FIG. 13B). At 1.5% formalin, the effect of amitriptyline on phase 1 flinches was not reversed in any experiment, while the effect on biting/licking was reversed only with the caffeine at 100 nmol amitriptyline (data not shown). Caffeine and CPT did not produce an intrinsic effect in the 1.5% formalin test (FIG. 13A–B), but caffeine produced a slight reduction in flinches at 2.5% formalin concentration as can be seen by comparing the data of (FIGS. 11A–C and FIGS. 12A–B).

Coadministration of $NH_2dAD$, an inhibitor of adenosine kinase, at a dose of 100 nmol augmented the action of a partially effective dose of amitriptyline on phase 2 flinches in a 2.5% formalin test (FIG. 14), but was without effect on phase 1 flinches and biting/licking time (data not shown). This dose of $NH_2dAD$ is without intrinsic effect on formalin behaviors at this concentration of formalin.

Figures 15A, 15B:
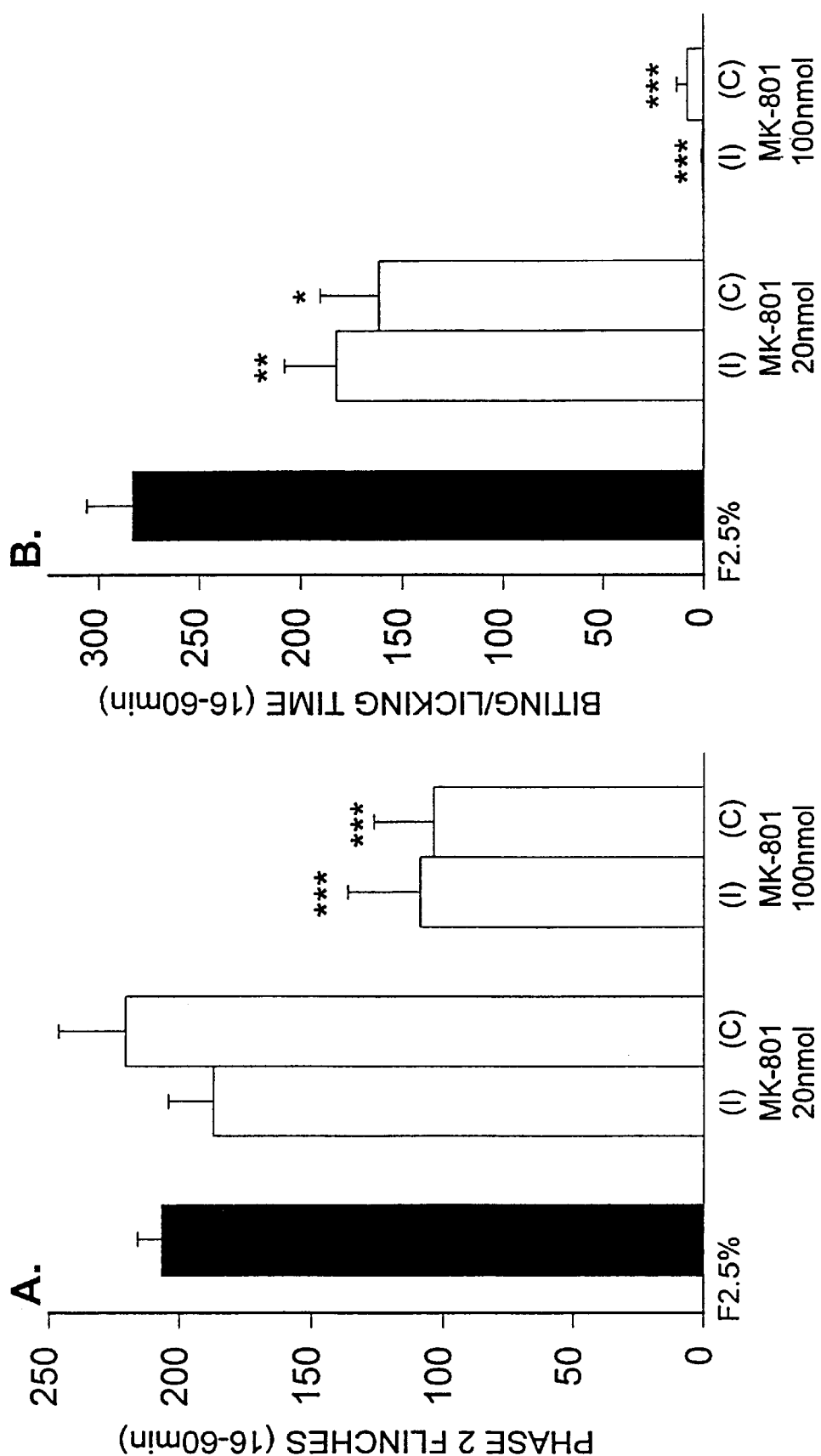
FIGS. 15A–B are bar graphs illustrating inhibition of responses by rats to 2.5% formalin (filled bars) when the formalin is coadministered with MK-801 (20 nM or 100 nM) (open bars) into the ipsilateral (I) paw, or the contralateral (C) paw. n=6–8 per group.
*=P<0.05; =P<0.01, and *=P<0.001 compared to formalin alone.

D. Involvement of Other Mechanisms in the Local Antinociceptive Action of Amitriptyline Amitriptyline is known to exert a number of pharmacological effects. Experiments were conducted to test for potential involvement of interactions with excitatory amino acid receptors, biogenic amines (noradrenaline, 5-hydroxytryptamine or 5-HT, histamine) and endogenous opioids by determining effects of respective receptor antagonists. The coadministration of the non-competitive NMDA receptor antagonist, MK-801 at doses of 20 and 100 nmol with formalin produced a dose-dependent reduction in phase 2 flinching behaviors and biting/licking time (FIGS. 15A–B), with the latter behavior exhibiting a greater sensitivity to inhibition. No significant effects were seen on phase 1 flinching behaviors (data not shown). This action of MK-801 is not locally mediated, as shown by the identical effect seen following administration of the MK-801 into the contralateral hindpaw (FIGS. 15A–B). These results indicate that MK-801 acts by a systemic route. Injection of 100 nmol (but not 20 nmol) into both the ipsilateral and contralateral hindpaws also produces a behavioral hyperactivity during the observation interval. Lower doses of MK-801 (0.03 and 0.3 nmol) coadministered with formalin had no effect on any parameter (n=4 each, data not shown).

Figure 16A:
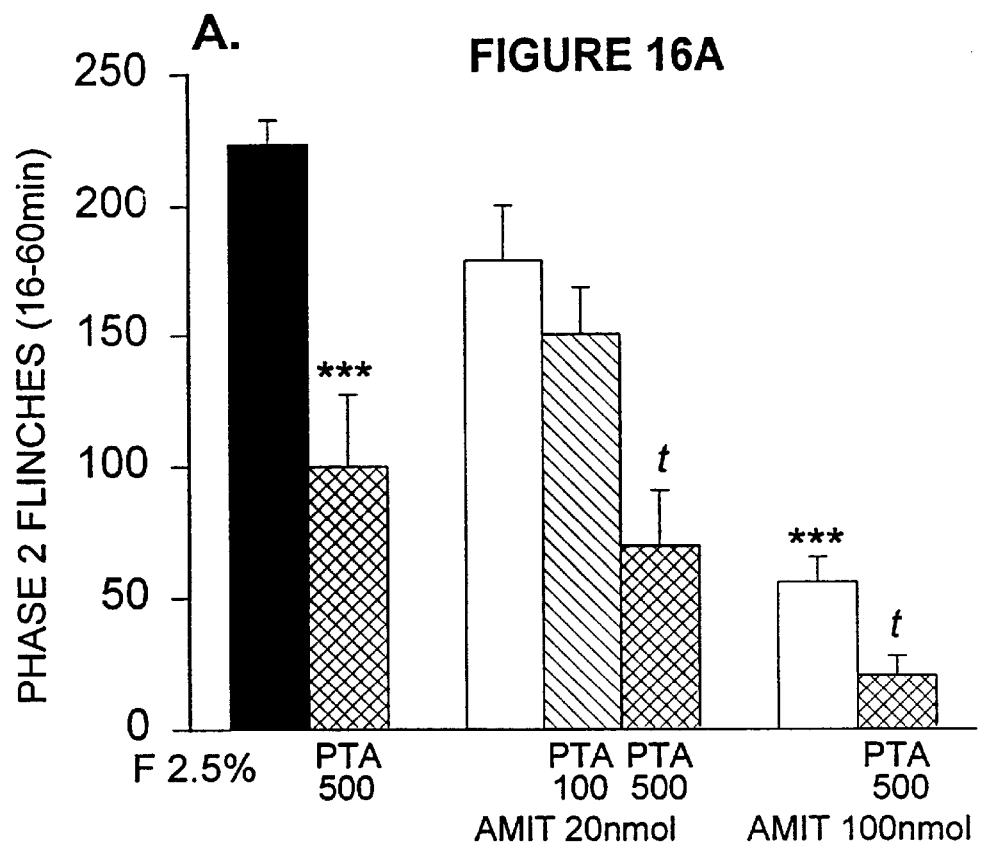
FIGS. 16A–B are bar graphs illustrating that the antinociceptive action of amitriptyline (20 nmol and 100 nmol) against 2.5% formalin (F) (dark bar) was not decreased by coadministration of phentolamine (PTA) (100 nmol and 500 nmol) (bars with crossed hatching) or naloxone (NLX) (100 nmol and 300 nmol) (bars with horizontal lines). n=5–8 per group.
*=P<0.05, ***=P<0.001 compared to the formalin group; t=P<0.05 compared to the formalin/amitriptyline combination.

Coadministration of phentolamine (PTA), a non-selective-adrenoreceptor antagonist, had no significant effect on the action of amitriptyline at 100 nmol, but coadministration of 500 nmol augmented its action (FIG. 16A). This potentiation is due to an additive action of an intrinsic effect of phentolamine with that of amitriptyline, as phentolamine alone at this dose inhibited the action of formalin (FIG. 16A). An identical pattern of interactions was seen with the phase 2 biting/licking time, but no significant effects were seen with phentolamine on phase 1 flinching (data not shown).

Figure 16B:
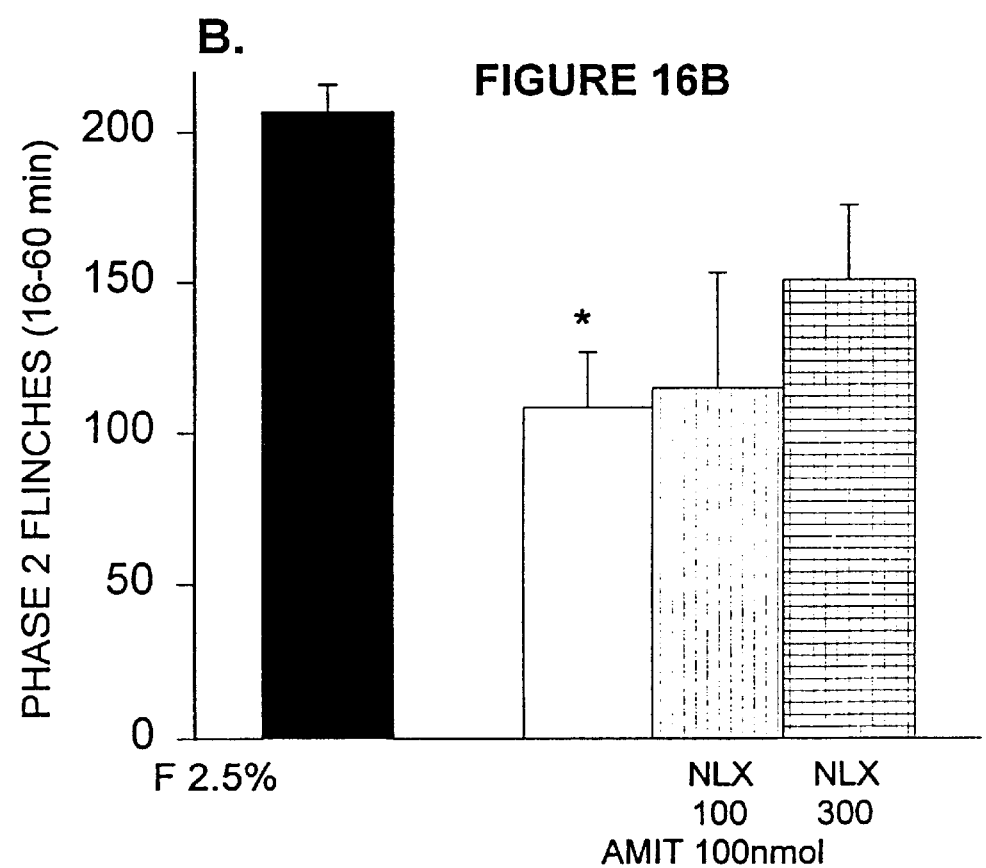

To examine a potential local antihistamine or antiserotonergic action for amitriptyline, tests were designed to determine whether amitriptyline could alter the flinching behaviors produced by $N^6$-benzyl NECA, an adenosine $A_3$ receptor agonist which produces intrinsic nociceptive behaviors by releasing histamine and 5-HT from mast cells. In these tests, 100 nmol amitriptyline did not alter the number of flinches generated by 5 nmol $N^6$-benzyl-NECA ($25.5 \mp 6.3$ flinches in the absence, and $27.8 \mp 4.3$ flinches in the presence of amitriptyline, n=6 per group). Naloxone, an opioid receptor antagonist, did not alter the local effect of amitriptyline against phase 2 flinching (FIG. 16B), phase 1 flinching, or biting/licking time (data not shown).

EXAMPLE 3

The drugs tested were desipramine, fluoxetine, caffeine and propranolol (Sigma Chemical Co., St. Louis, Mo.), ketanserin and tropisetron (Research Biochernicals Inc., Natick, N.J.), and GR113808A (Glaxo Research Group, Greenford, Middlesex, U.K.). Formalin (37% formaldehyde) (British Drug Houses, Toronto, Ontario) was the control irritant. All drugs were prepared in saline and diluted to the indicated dose with formalin when coinjected.

Rats were maintained and surgically altered by spinal nerve ligation of the 5th and 6th spinal nerves as described in Example 1. Preliminary tests showed that the spinal ligation surgery generates a thermal hyperalgesia of 2–3 sec in the paw corresponding to the ligation (baseline on non-ligated side 10–12 sec, and 710 on ligated side), and this effect was maintained for at least 22 days following surgery.

A. The Formalin Test

The formalin test was applied as described in Example 2 above. Following injections, rats were returned to the observation chamber and scored for flinching behaviours (lifting, shaking or rippling of the haunch) and biting/licking time.

Two rats in adjacent chambers were observed at a time, with observations occurring in alternate 2 min bits. Recorded episodes were not corrected for this, so values represent about half of the total behaviours expressed.

B. Local Antinociceptive Action of Desipramine and Fluoxetine

Figure 17A:
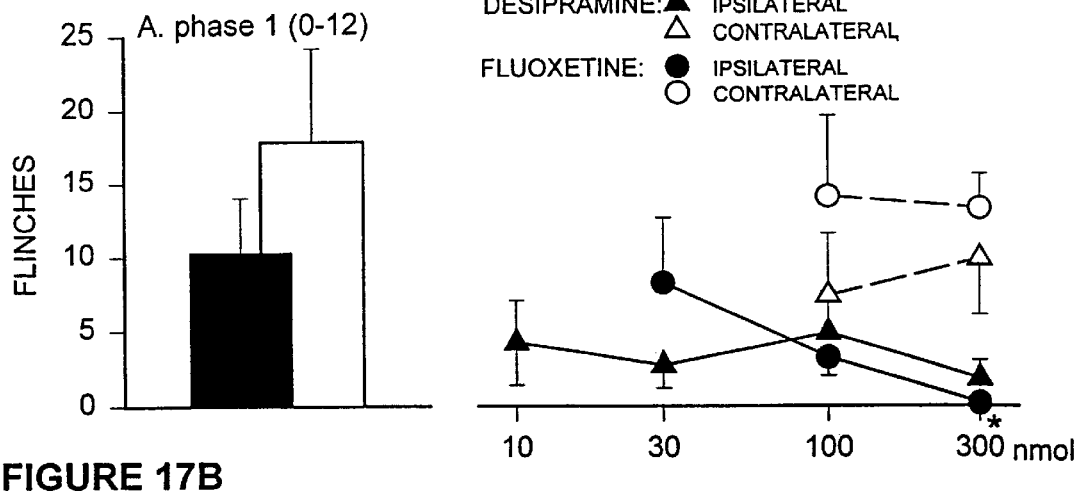
FIGS. 17A–C are a series of graphs showing dose-related inhibition of formalin-induced pain response behaviors by locally administered tricyclic antidepressants. The bar graphs depict the control values for formalin (solid bar) and saline (open bar) when injected contralaterally; while the dosage graphs depict the results when antidepressant, rather than control, is injected.
Figure 17B:
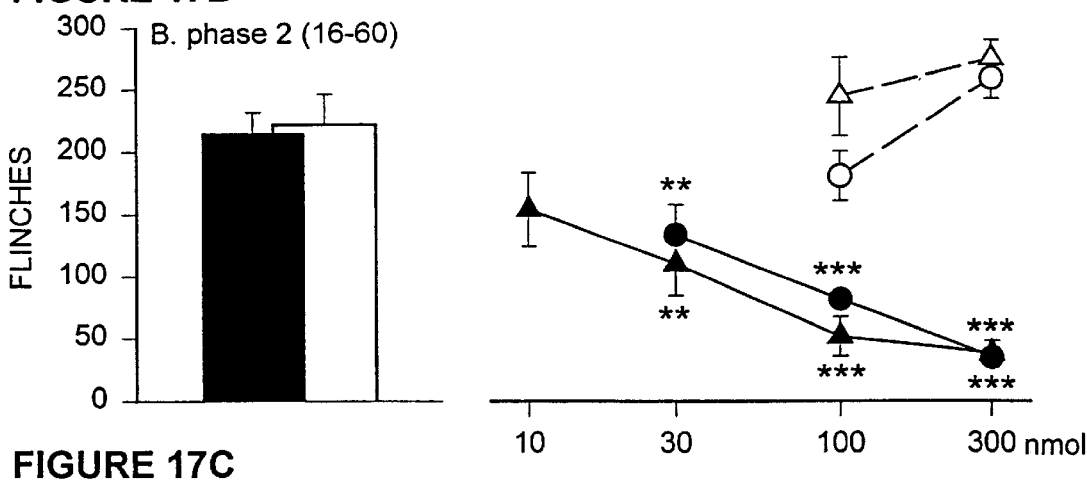
Figure 17C:
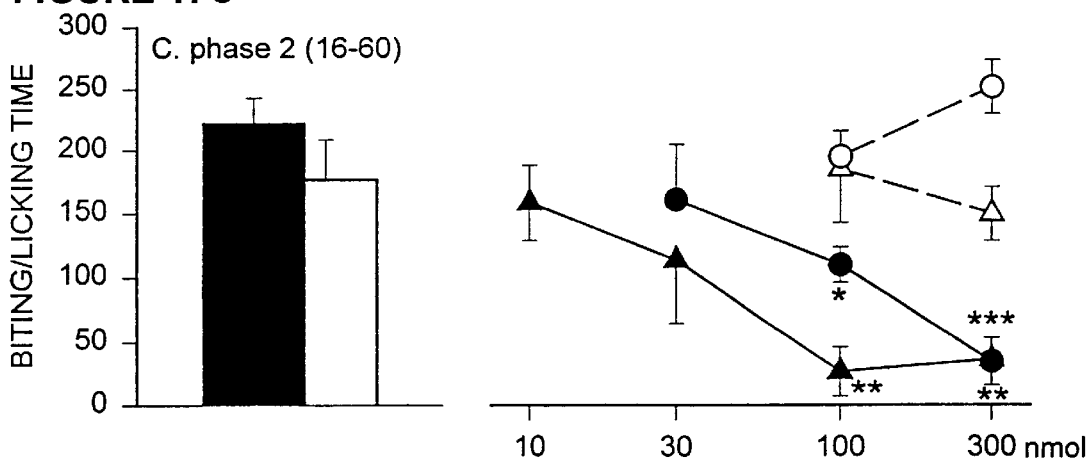
Figure 18A:
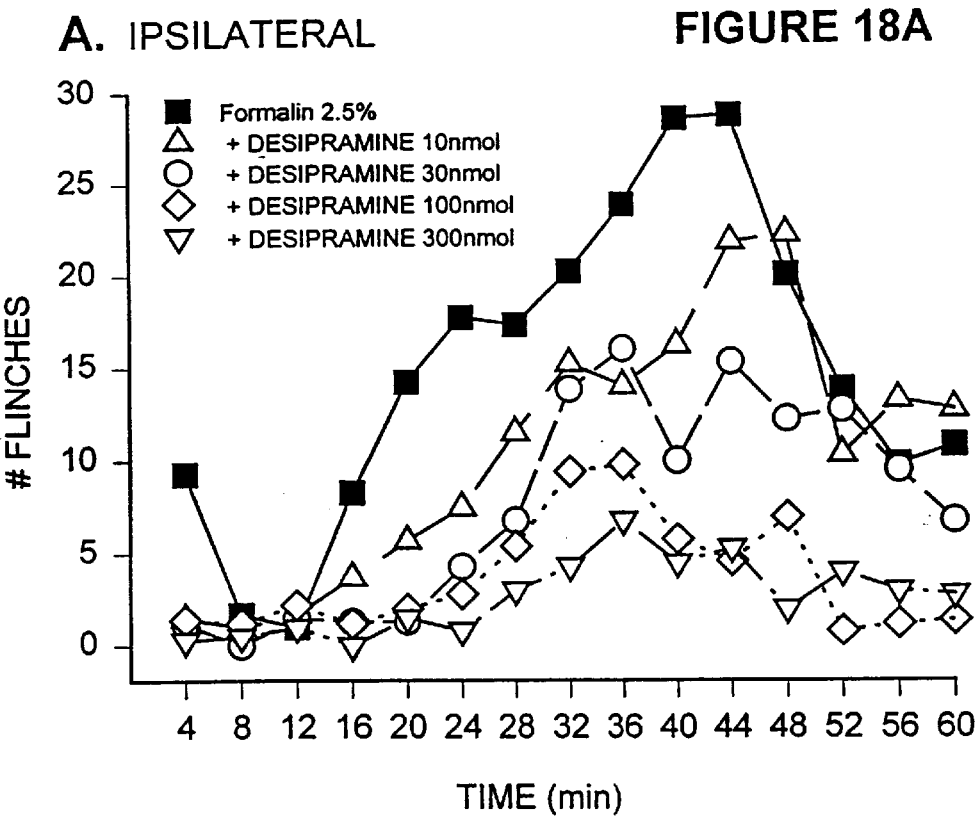
FIGS. 18A–D are a series of graphs illustrating the suppression of pain related behaviors by coadministration of desipramine with 2.5% formalin.
Figure 18B:
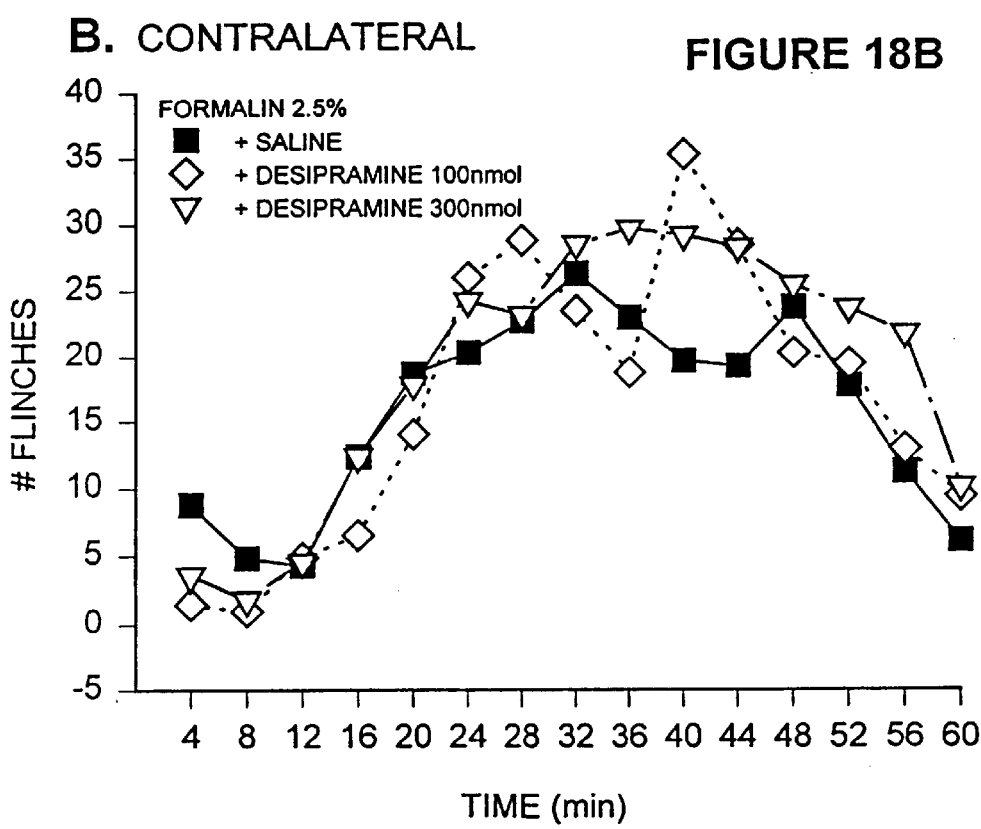
Figure 18C:
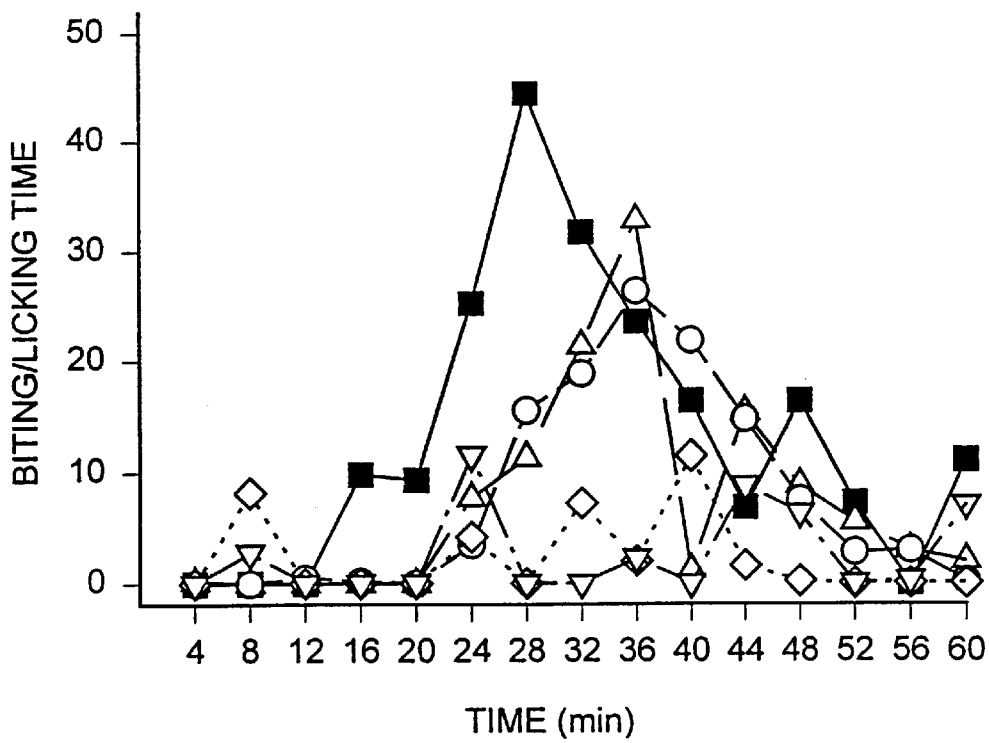
Figure 18D:
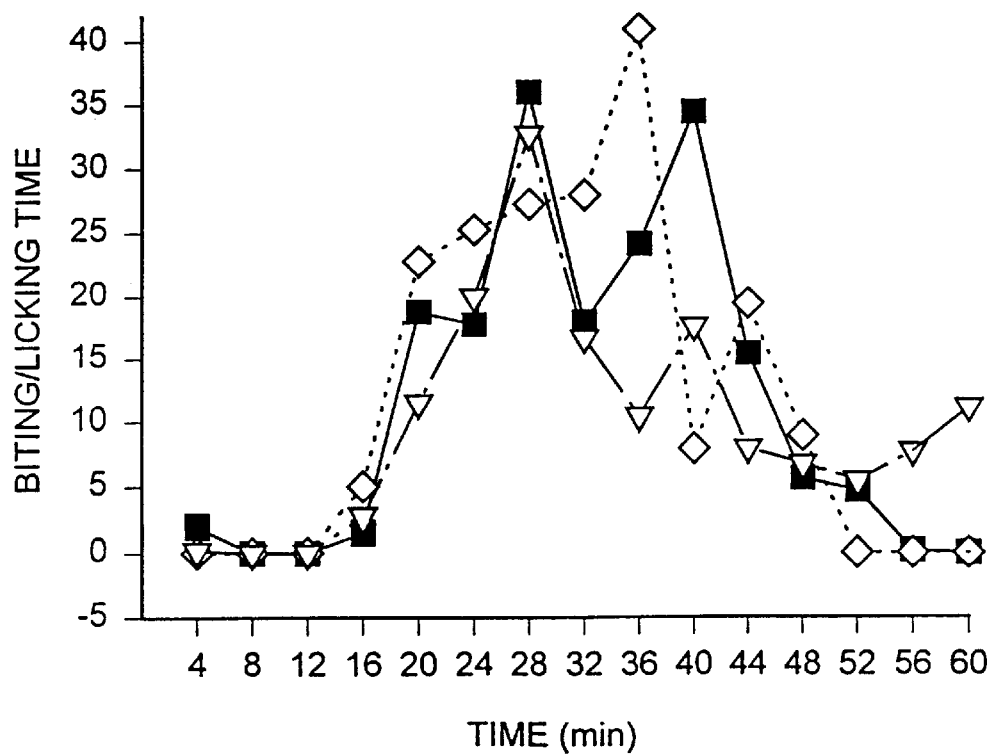

When independently injected with formalin 2.5% into the dorsal hindpaw of a non-surgically altered rat, desipramine (10–300 nmol) and fluoxetine (30–300 nmol) both produced a dose-dependent antinociceptive action against phase 2 flinching behaviours (FIG. 17B) and phase 2 biting/licking behaviours (FIG. 17C). Phase 1 flinching behaviours exhibited much more variability, and were only reduced significantly at the highest doses (FIG. 17A). There was no phase 1 expression of biting/licking behaviours (FIG. 18C). Desipramine action suppressed both pain response behaviours (illustrated in FIGS. 18A–B) in a uniform manner throughout the entire time course observed. A similar pattern of suppression of behaviours was observed with fluoxetine (data not shown). However, when the doses that were most efficacious in the ipsilateral paw were injected into the contralateral hindpaw, the antinociceptive action resulting from coadministration of desipramine or fluoxetine with formalin was not observed. (FIGS. 17A–C, 18B and 18C). These results show that the antinociceptive effect of the locally injected antidepressant was local only.

C. Coadminisration of Desipramine or Fluoxetine and Caffeine

Figure 20A:
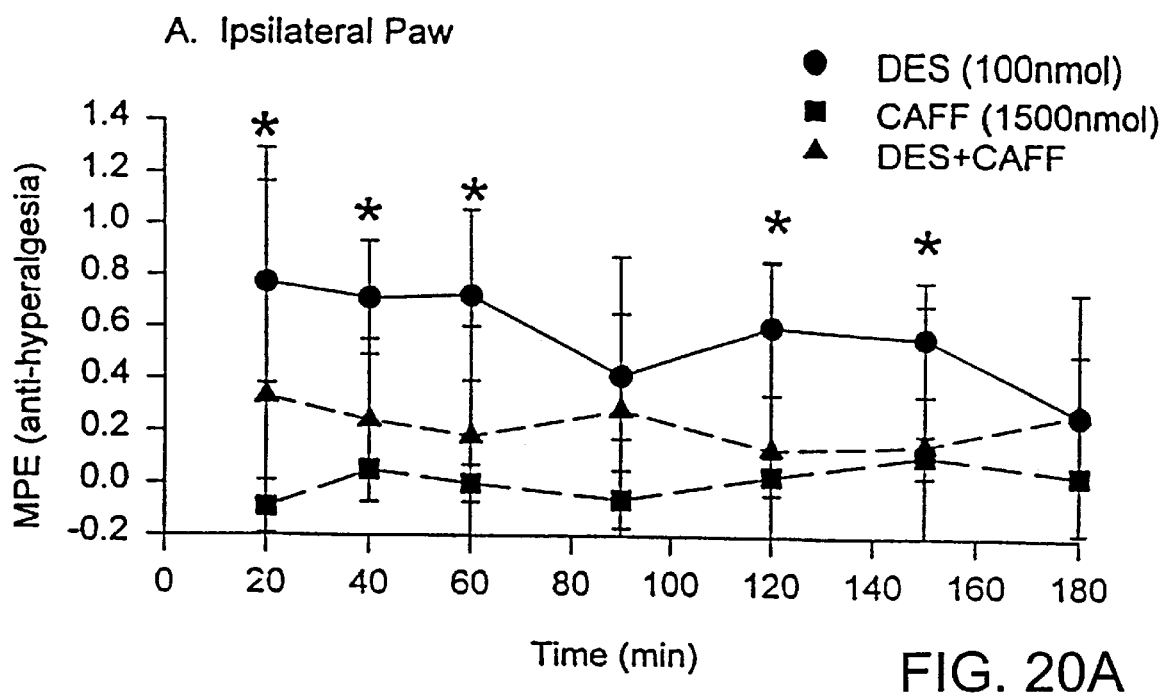
FIGS. 20A–B are two graphs illustrating the effect of caffeine (1500 nmol) (CAFF) for inhibiting the antinociceptive effect of desipramine when coadministered into the paw ipsilateral to spinal ligation.
Figure 20B:
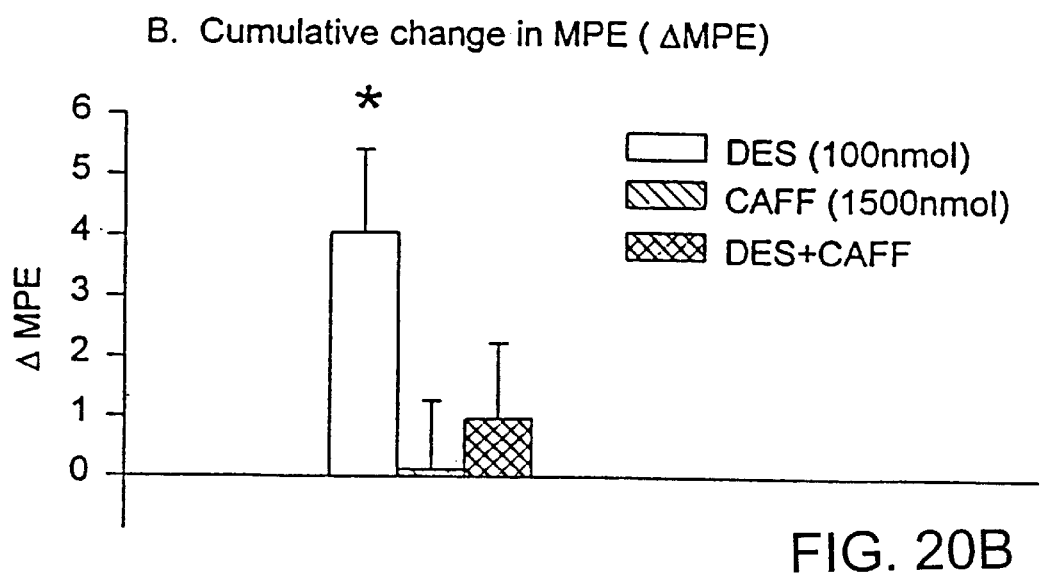

To test the effect of caffeine on the antinociceptive effect of the antidepressant drugs, a formalin concentration of 1.5% was used as this concentration revealed the involvement of adenosine in the action of amitriptyline most clearly. (See Example 2 above). Coadministration of caffeine (1500 nmol) with desipramine or fluoxetine had no significant effect on the antinociceptive actions of the antidepressants in any aspect of the formalin test (FIGS. 20A–C).

D. Local Administration of Desipramine and Fluoxetine in thermal hyperalgesia test Nerve damaged rats (SNL) were anaesthetized briefly for drug injections (in 50 μl) into the dorsal part of the hindpaw, either on the side ipsilateral to the surgery (ligated side) to test for local effects, or the contralateral side to test for systemically mediated effects. Thermal thresholds were determined with the investigator unaware of the particular treatment.

Figure 19A:
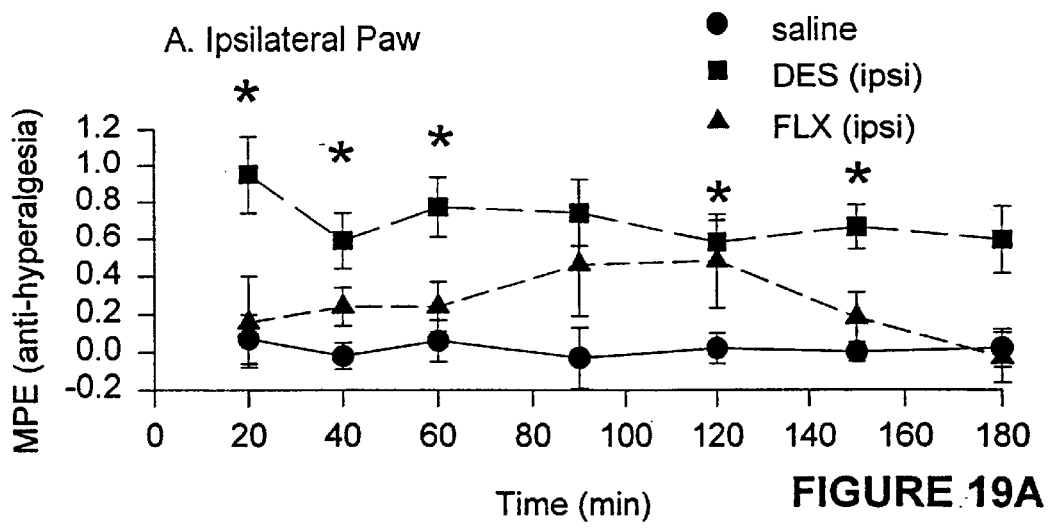
FIGS. 19A–C are a series of graphs illustrating the results of local injection of desipramine (DES) (100 nmol) and fluoxetine (FLX) (100 nmol).
Figure 19B:
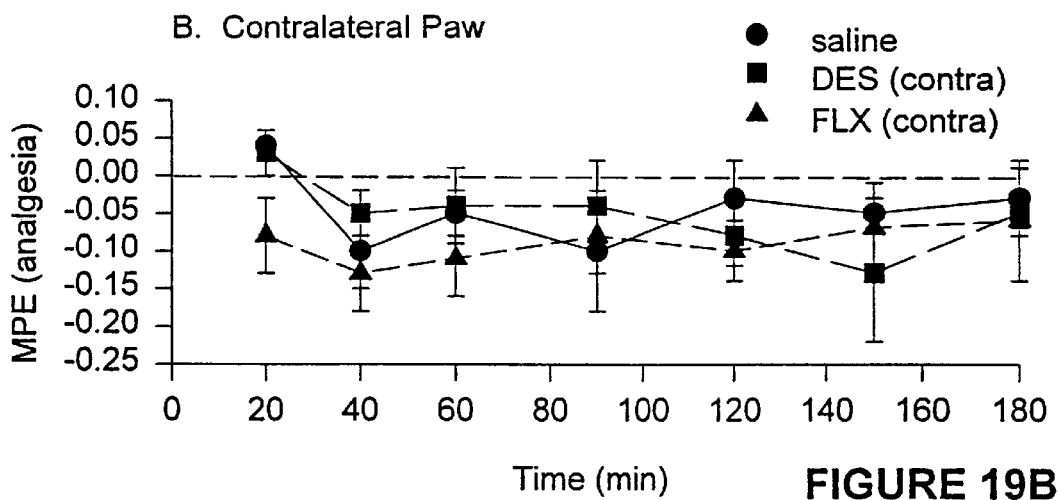
Figure 19C:
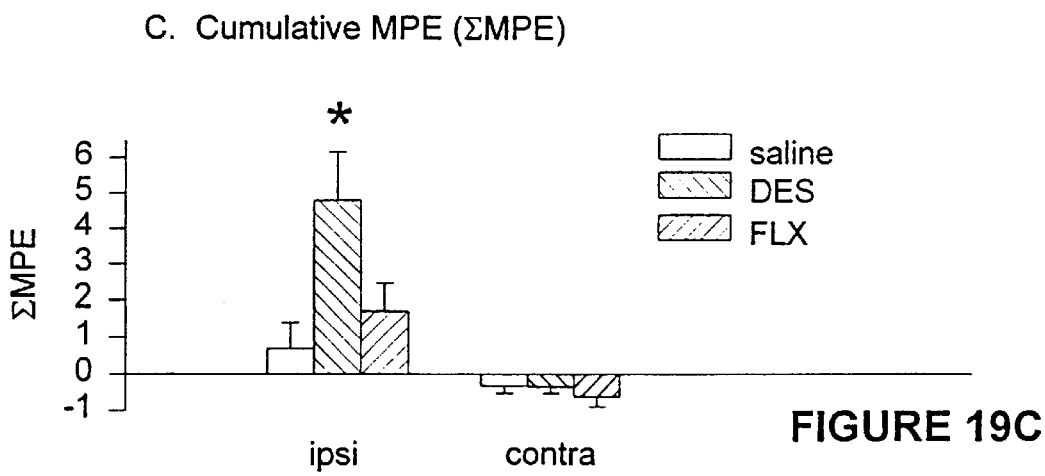
Figure 21A:
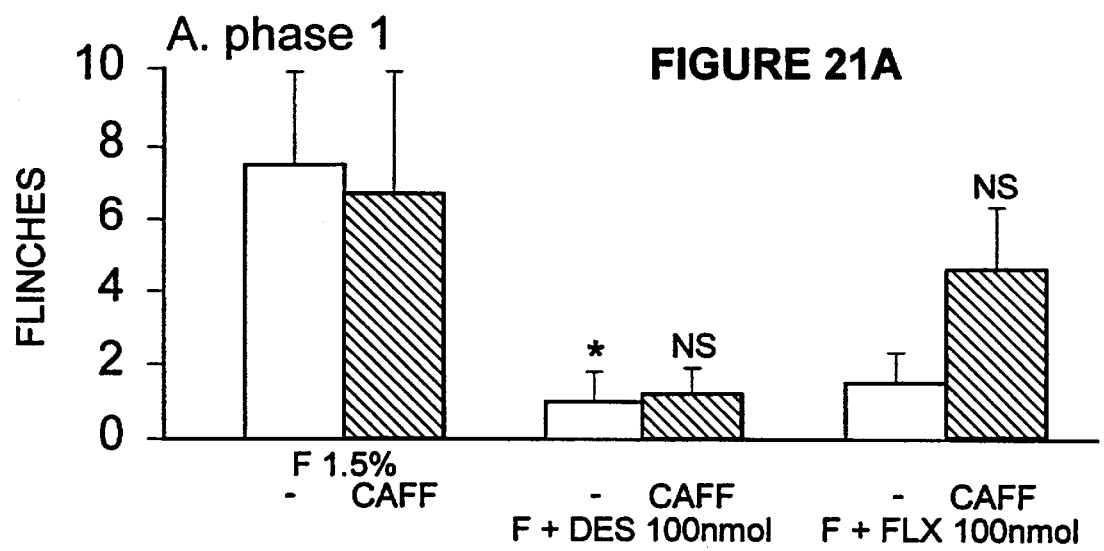
FIGS. 21A–C are a series of graphs showing a lack of suppression of the local antinociceptive effect of desipramine (DES) or fluoxetine (FLUOX) caused by coadministration of caffeine (CAFF) (1500 nmol) in the 1.5% formalin test.
Figure 21B:
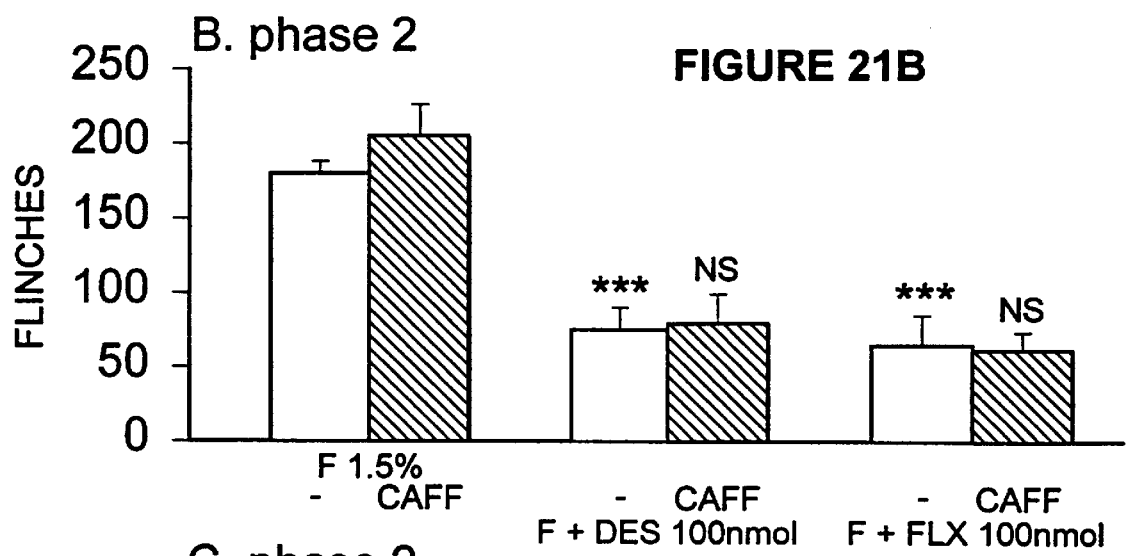
Figure 21C:
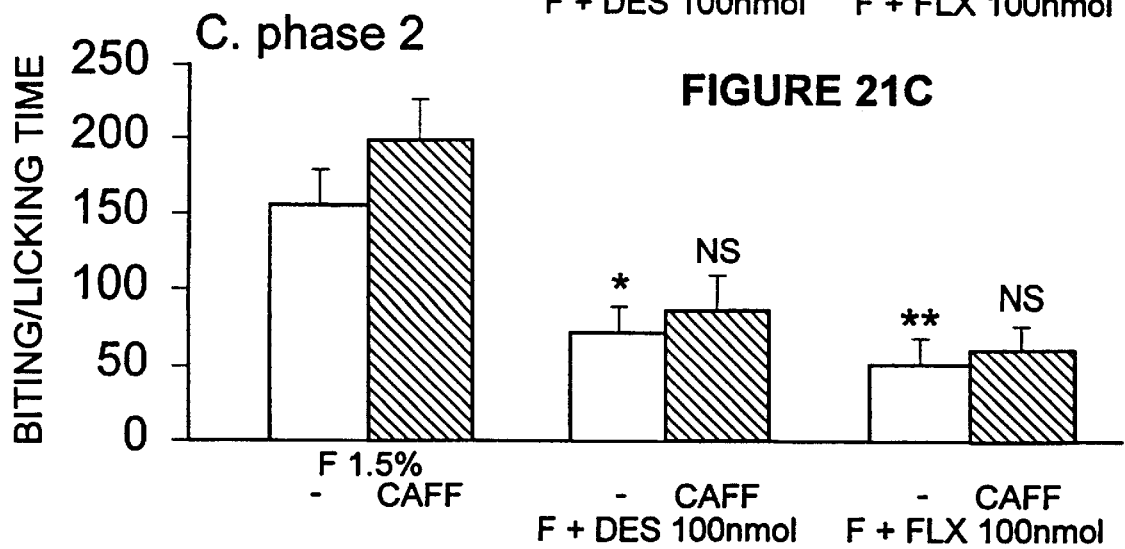

The local administration of desipramine (100 nmol), but not fluoxetine (100 nmol), into the hindpaw corresponding to the operated side produced a local anti-hyperalgesic effect when reaction thresholds were determined using a thermal paw stimulator (FIGS. 19A and 4B). This effect was not observed following injection into the contralateral paw corresponding to the non-operated side (FIG. 19B) These results show that the antinociceptive effects observed in the ipsilateral side were local. The local injection of desipramine or fluoxetine, 100 nmol each, into a normal rat paw (control) had no effect on thermal thresholds (n=4 each, data not shown). Coadministration of caffeine (1500 nmol), which inhibits the local action of amitriptyline on thermal hyperalgesia following spinal nerve ligation (Example 1), also blocked the antihyperalgesic action of desipramine in the spinal nerve ligation model (FIGS. 21A–C).

E. Effects of Desipramine, Fluoxetine and Amitriptyline on Paw Volume

Paw volume was determined by plethysmometry using a commercially available device (Ugo, Basile). The hindpaw was inserted into the solution to the junction of the hairy and non hairy skin, and volume was determined by displacement. Triplicate baseline determinations were determined prior to the formalin injection, and again immediately following the behavioral observation interval, which lasted 60 min. For time course determinations, volumes were determined at 30 min intervals as indicated up to 3 hours in separate groups of rats.

Figure 23A:
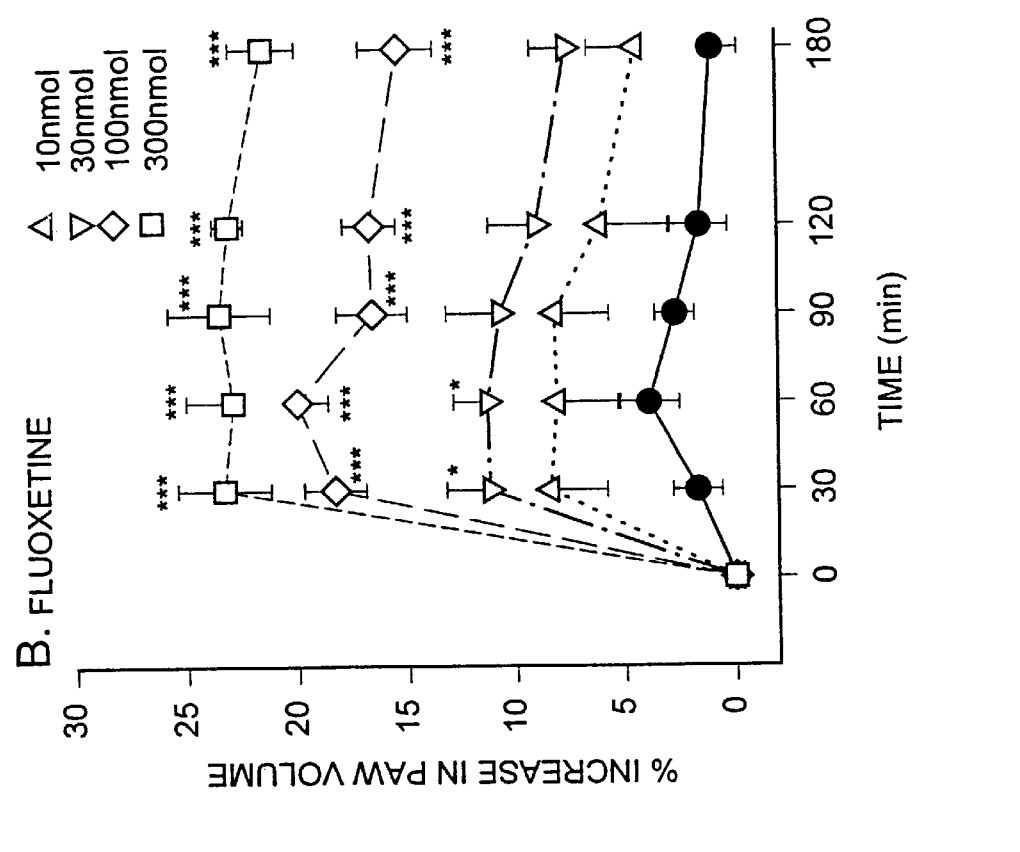
FIGS. 23A–C are a series of graphs illustrating the effects of desipramine, fluoxetine, and amitriptyline as compared with saline control on paw volume when injected into the dorsal hindpaw of the rat.
Figure 23B:
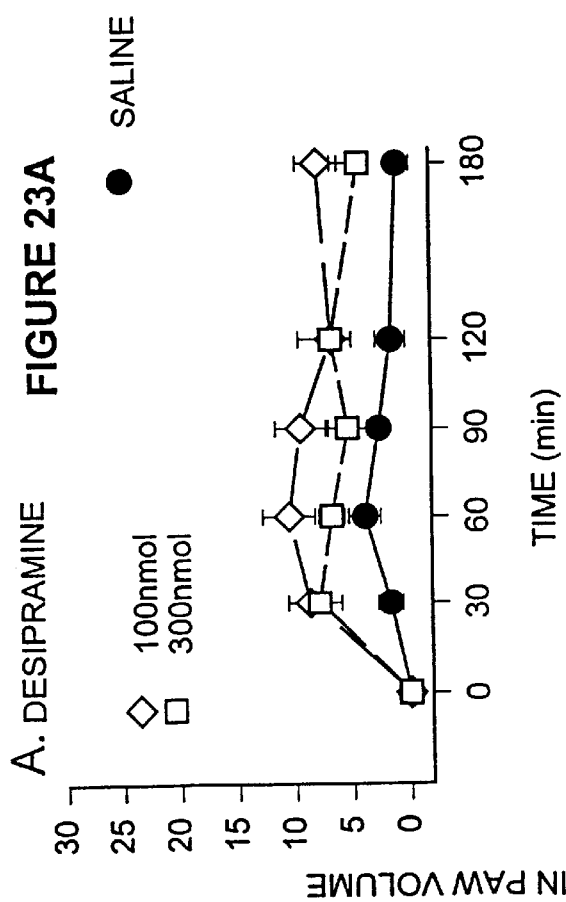
Figure 23C:
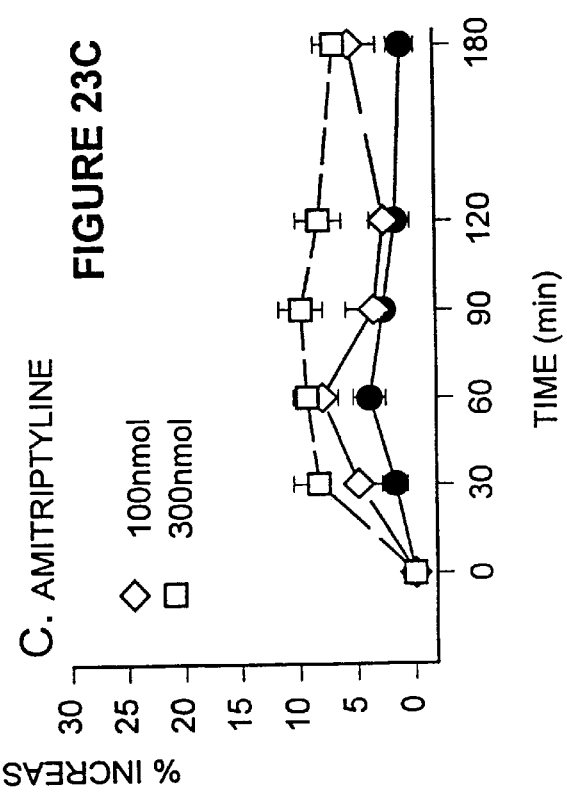

The anti-inflammatory effect of desipramine and fluoxetine was tested by the independent coadministration of desipramine and fluoxetine (doses of 100 or 300 nmol) with formalin. No significant effect on the increase in paw volume induced by 1.5% formalin alone was observed by the antidepressants, although there was a tendency towards an increased paw volume resulting from fluoxetine (FIG. 22A) at 2.5% formalin. When administered into the contralateral hindpaw, fluoxetine also significantly increased the paw volume in the absence of an inflammatory stimulus (FIG. 22B). The time course of the actions of desipramine and fluoxetine was also determined. In these tests desipramine produced a limited effect on paw volume (FIG. 23A), but fluoxetine produced a clear dose-related increase in paw volume that was maintained for the entire 3 hr observation interval (FIG. 23B). The increase in paw volume was not accompanied by a reddening of the paw, or by spontaneous behaviours indicative of discomfort (e.g. lifting, licking, shaking). Amitriptyline also produced a limited increase on paw volume (FIG. 23C), and did not significantly alter the degree of paw swelling produced by formalin 1.5% (data not shown).

F. Effects of Receptor Subtypes in Nociceptive Action of Desipramine and Fluoxetine To test for involvement of 5-HT receptor subtypes in the action of fluoxetine (100 nmol), the effects of propranolol (5-HT$_1$ receptor antagonist) (300 nmol), ketanserin (5-HT$_2$ receptor antagonist) (500 nmol), tropisetron (5-HT$_{3/4}$ receptor antagonist) (300 nmol), and GR113808A (5-HT$_4$ receptor antagonist) (500 nmol) on paw volume were determined at doses known to block 5-HT actions when injected into the hindpaw (G. J. Doak and J. Sawynok (1997) Neuroscience 80:939–949). The results of these tests show that the increase in paw volume induced by fluoxetine was blocked by ketanserin but not by any of the other antagonists, indicating an involvement of 5-HT$_2$ receptor subtypes in this action (FIGS. 24A–B).

It will be apparent to those skilled in the art that various changes may be made in the invention without departing from the spirit and scope thereof, and therefore, the invention encompasses embodiments in addition to those specifically disclosed in the specification, but only as indicated in the appended claims.

That which is claimed is:

1. A method for producing local analgesia in a subject having a site of local discomfort, said method comprising locally administering an effective amount of an antidepressant to the site.

2. The method according to claim 1 wherein the antidepressant is a tricyclic antidepressant.

3. The method according to claim 2 wherein the tricyclic antidepressant has a structure:

wherein Z is a 7-membered ring, optionally containing 1 or 2 biocompatible heteroatoms, or an 8-membered bicyclic ring, Ar$_1$ and Ar$_2$ are optionally substituted aromatic rings fused to Z, and R is an alkylamino or arylamino substituent, optionally an N-oxide derivative thereof.

4. The method according to claim 3 wherein the heteroatom is oxygen or nitrogen.

5. The method according to claim 3 wherein $Ar_1$ and $Ar_2$ are independently optionally substituted with a biocompatible halogen.

6. The method according to claim 3 wherein the alkylamino or arylamino substituent is an N-oxide derivative thereof.

7. The method according to claim 3 wherein the alkylamino substituent comprises from 4 to 5 carbons atoms.

8. The method according to claim 7 wherein the alkylamino is a tertiary or secondary amino group.

9. The method according to claim 3 wherein R is selected from the group consisting of

-$(CH_2)_3N(CH_3)_2$,

-$(CH_2)_3NHCH_3$,

-$CH_2CH(CH_3)CH_2N(CH_3)_2$,

=$CH(CH_2)_2N(CH_3)_2$,

=$CH(CH_2)_2NHCH_3$.

10. The method according to claim 2 wherein the tricyclic antidepressant is selected from the group consisting of clomipramine, imipramine, amitriptyline, doxepin, desipramine, nortriptyline, amoxapine, maprotiline, trimipramine, and suitable combinations of any two or more thereof.

11. The method according to claim 2 wherein the tricyclic antidepressant is amitriptyline or desipramine.

12. The method according to claim 1 wherein the antidepressant is a second generation or third generation antidepressant.

13. The method according to claim 12 wherein the second generation or third generation antidepressant has the structure $Ar_3(Y)-X-Ar_4(Q)$ wherein:

$Ar_3$ is an N-containing heterocyclic ring,

Y is either an aryl group fused to the heterocyclic ring or one or two substituents selected from alkyl, arylalkyl, arylalkyloxy, aryl and heteroaryl substituents comprising a total of about 4 to 8 carbons attached to $Ar_3$, X is a 2 to 5 carbon alkyl group linking $Ar_3$ and $Ar_4$, $Ar_4$ is a piperazine attached to X by a first nitrogen atom of $Ar_4$, and Q is a benzene ring optionally substituted with a biocompatible halogen, and attached to $Ar_4$ at a second nitrogen atom of $Ar_4$.

14. The method according to claim 13 wherein X is a 3 carbon alkyl group.

15. The method according to claim 13 wherein $Ar_3$ is a 1,2,4-triazine, Y is an arylalkyloxy substituent containing 6 to 8 carbon atoms, and is substituted at the 4 position of $Ar_3$.

16. The method according to claim 13 wherein Y is a 3 carbon alkyl substituent.

17. The method according to claim 13 wherein the benzene ring is substituted with a halogen selected from the group consisting of chlorine, bromine, and fluorine.

18. The method according to claim 2 wherein the tricyclic-antidepressant is desipramine.

19. The method according to claim 2 wherein the tricyclic-antidepressant is amitriptyline.

20. The method according to claim 2 wherein the tricyclic-antidepressant is administered topically.

21. The method according to claim 1 wherein the antidepressant is administered as a formulation selected from the group consisting of a cream, a lotion, a gel, an ointment, a spray, a polymer stabilized crystal, a powder, and an aerosol.

22. The method according to claim 1 wherein the antidepressant is administered by injection.

23. The method according to claim 1 wherein the antidepressant is administered encapsulated in a delivery system selected from the group consisting of a microsphere, a polymer stabilized crystal, and a liposome.

24. The method according to claim 1 wherein the analgesia suppresses pain caused by inflammation.

25. The method according to claim 1 wherein the analgesia suppresses neuropathic pain.

26. The method according to claim 1 wherein the antidepressant is administered by supersonic powder injection or transdermal electroporation.

27. The method according to claim 12 wherein the second generation or third generation antidepressant is administered topically.

28. The method according to claim 12 wherein the second generation or third generation antidepressant is administered as a formulation selected from a cream, a lotion, a gel, an ointment, a spray, a polymer stabilized crystal, a powder, or an aerosol.

29. The method according to claim 12 wherein the second generation or third generation antidepressant is administered by injection.

30. The method according to claim 12 wherein the second generation or third generation antidepressant is administered by supersonic powder injection or transdermal electroporation.

31. The method according to claim 12 wherein the antidepressant is administered encapsulated in a delivery system selected from a microsphere, a polymer stabilized crystal, or a liposome.

32. The method according to claim 12 wherein the analgesia suppresses pain caused by inflammation.

33. The method according to claim 12 wherein the analgesia suppresses neuropathic pain.

34. The method according to claim 12 wherein the second generation or third generation antidepressant is mirtazapine, venlafaxine, trazodone, bupropion, fefazodone, or suitable combinations of any two or more thereof.

* * * * *